US012805822B2

(12) United States Patent
Liu

(10) Patent No.: US 12,805,822 B2
(45) Date of Patent: Nov. 24, 2026

(54) SYSTEMS AND METHODS OF BODY MOTION MANAGEMENT DURING NON-INVASIVE IMAGING AND TREATMENT PROCEDURES

(71) Applicant: Rui Liu, Augsburg (DE)

(72) Inventor: Rui Liu, Augsburg (DE)

( * ) Notice: Subject to any disclaimer, the term of this patent is extended or adjusted under 35 U.S.C. 154(b) by 1150 days.

(21) Appl. No.: 17/393,226

(22) Filed: Aug. 3, 2021

(65) Prior Publication Data

US 2022/0047237 A1 Feb. 17, 2022

Related U.S. Application Data

(60) Provisional application No. 63/063,257, filed on Aug. 8, 2020.

(51) Int. Cl.

| | |
|---|---|
| ***A61B 6/00*** | (2024.01) |
| ***A61B 6/03*** | (2006.01) |
| ***A61B 6/04*** | (2006.01) |
| ***A61B 8/00*** | (2006.01) |
| ***A61B 8/08*** | (2006.01) |
| ***A61B 17/00*** | (2006.01) |
| ***G16H 20/30*** | (2018.01) |
| ***G16H 20/40*** | (2018.01) |
| ***G16H 30/20*** | (2018.01) |
| ***G16H 40/67*** | (2018.01) |
| ***G16H 50/20*** | (2018.01) |

(52) U.S. Cl.

CPC ............ *A61B 6/527* (2013.01); *A61B 6/0407* (2013.01); *G16H 20/30* (2018.01); *G16H 40/67* (2018.01); *A61B 8/5276* (2013.01); *A61B 2017/00699* (2013.01); *A61B 2017/00703* (2013.01)

(58) Field of Classification Search

CPC .................. A61B 6/527; A61B 6/0407; A61B 2017/00699; A61B 2017/00703; A61B 8/5276; A61B 6/032; A61B 8/085; A61B 6/541; A61B 6/0485; G16H 20/30; G16H 40/67; G16H 20/40; G16H 30/20; G16H 50/20

See application file for complete search history.

(56) References Cited

U.S. PATENT DOCUMENTS

| | | | |
|---|---|---|---|
| 7,953,204 B2 | 5/2011 | Sumanaweera et al. | |
| 7,983,743 B2 | 7/2011 | Rudy et al. | |
| 9,655,561 B2 | 5/2017 | Tilk et al. | |
| 10,727,010 B1 * | 7/2020 | Henke .................... | G01R 31/40 |

(Continued)

OTHER PUBLICATIONS

Cardioinsight Mapping Vest, Medronic, https://europe.medtronic.com/xd-en/healthcare-professionals/products/cardiacd-rhythm/cardiac-mapping/cardioinsight-mapping-vest.html; 6 pages, (Jul. 8, 2021).

(Continued)

*Primary Examiner* — Carrie R Dorna
*Assistant Examiner* — Joshua Daryl D Lannu
(74) *Attorney, Agent, or Firm* — The Marbury Law Group, PLLC

(57) ABSTRACT

A non-invasive system for concurrent monitoring cardiac, respiration activity and other body motions from a patent support device integrated with biometric sensors. Such system can also predicate a motion state to enable/disable a medical imaging device or radiotherapy device during cancer and/or cardiac arrhythmias treatment.

31 Claims, 13 Drawing Sheets

(56) References Cited

U.S. PATENT DOCUMENTS

| | | | | |
|---|---|---|---|---|
| 2012/0289759 | A1* | 11/2012 | Lynch | A61F 5/37 128/870 |
| 2012/0310053 | A1* | 12/2012 | Henning | A61B 5/086 600/407 |
| 2013/0281814 | A1* | 10/2013 | Tilt | A61B 5/282 600/382 |
| 2015/0282768 | A1* | 10/2015 | Luna | A61B 5/0205 600/386 |
| 2016/0015290 | A1* | 1/2016 | Kim | A61B 5/7225 600/547 |
| 2016/0074674 | A1 | 3/2016 | Kohli et al. | |
| 2017/0116387 | A1* | 4/2017 | El-Zehiry | G06T 7/11 |
| 2018/0318606 | A1* | 11/2018 | Robinson | A61B 8/5261 |
| 2019/0231083 | A1* | 8/2019 | Hsu | A61G 7/05776 |
| 2020/0086078 | A1* | 3/2020 | Poltorak | A61N 2/006 |
| 2020/0179722 | A1* | 6/2020 | Packer | A61N 5/1037 |
| 2020/0346034 | A1 | 11/2020 | Garonna et al. | |

OTHER PUBLICATIONS

SecureVac Immobilization System, www.bionix.com, 2021 Bionix LLC, MKT-0019, Rev. B.

* cited by examiner

SYSTEMS AND METHODS OF BODY MOTION MANAGEMENT DURING NON-INVASIVE IMAGING AND TREATMENT PROCEDURES

RELATED APPLICATIONS

This application claims the benefit of priority to U.S. Provisional Application No. 63/063,257, filed on Aug. 8, 2020, the entire contents of which are incorporated by reference herein for all purposes.

FIELD

This disclosure relates generally to radiation therapy or radiotherapy. More specifically, this disclosure relates to non-invasive systems and methods for managing patient motion.

BACKGROUND

Radiotherapy has been employed to treat cancer tumours and cardiac arrhythmias. During radiation therapy, a high-energy beam is applied from an external source towards a target that may be located inside a patient's body. Such high-energy beam (typically megavoltage X-rays), for example, could be generated by a linear accelerator (LINAC) which produces a collimated radiation beam that is directed into the target. Other types of radiotherapy may deliver particles such as beams of electrons, positrons, neutrons or protons to the target.

One problem that can interfere with treatment effectiveness is that target tissues may move. For example, a tissue may move with cardiac activity and/or respiration activity and/or unexpected body motion such as a cough. Such motions become problematic when treating tumors of the lung, breast, pancreas and liver, as the motion may introduce radiation dosage on the heathy tissue surrounding the target treatment area. Also, when using radiation for cardiac arrhythmias treatment, the heart moves according to the cardiac motion, making targeting of particular locations of the heart challenging for radiation therapy.

Some radiotherapy techniques include using an invasive surgical procedure to insert fiducial markers close to target treatment areas such that those markers are visible within X-Ray images and can be used to trigger the radiation beam during treatment. However, such markers do not provide comprehensive accounting of motion of normal tissues adjacent to tumours. Moreover, the implanted markers normally generate local image artifacts under magnetic resonance imaging (MRI) and can create difficulty in image-based diagnosis interpolation.

SUMMARY OF THE DISCLOSURE

The present disclosure relates to non-invasive systems and methods for monitoring cardiac activity and/or respiration activity and/or other body motions. Embodiments of the present disclosure include a system for monitoring a body motion state of a patient that includes a patient support device including at least one sensor for measuring biometric data of a patient located on the patient support device, and a processor, operatively coupled to an active medical device and the at least one sensor of the patient support device, the processor containing processor-executable instructions configured to perform operations including generating a control signal to control an operation of an active medical device based on the biometric data measured by the at least one sensor, where the biometric data indicates a body motion state of the patient.

In various embodiments, the active medical device includes one or more of a magnetic resonance imaging (MRI) device, an X-ray device, a computed tomography (CT) device, an ultrasonography device, a radiotherapy device, a shockwave generator, a positron emission tomography (PET) device, an ElectroCardioGraphic imaging (ECGi) device, and a high-intensity focused ultrasound device.

According to various embodiments of the disclosure, a non-invasive system may include a patient support device that is located under the patient's body and above a patient table. The patient support device may include one or more sensors to provide biometric data of cardiac activity and/or respiration activity and/or other body motion.

According to an embodiment of the disclosure, the patient support device may include a soft material which provides certain comfort to the patient. In addition or alternatively, the patient support device may include a moldable vacuum cushion comprising a flexible bag of gas-impermeable material. The material(s) of the patient support device may be non-conductive and transparent to a medical imaging device such as a CT device and/or an MRI device such that the patient support device will not generate unacceptable image artifacts which could result in an incorrect diagnosis or incorrect treatment planning. In various embodiments, a patient support including a vacuum cushion may be molded to the patient's anatomy and may allow the patient to be positioned in exactly the same position for medical imaging and treatment and for each subsequent treatment session.

According to an embodiment of the invention, a patient support device including a moldable vacuum cushion may include a skin-electrode interface array located at predefined positions for measuring multiple electronic potentials and/or bio-impedance signals across a patient's body. Since the vacuum cushion may be molded to the patient's outline shape and may allow the patient to be repeatedly positioned in the same position, the readout of measured bio-impedance may be highly reproducible. This is in contrast to the conventional procedure in which electrodes are manually attached at estimated body positions, which is generally non-reproducible and time consuming.

According to an embodiment of the invention, the interconnections to each skin-electrode interface may include flexible PCB/cables that may be located inside of the patient support device and/or printed conductive signal traces on the inside surface of a cover of the patient support device. An advantage of using flexible cable and/or printed trace interconnects is that such interconnects may be deformed with a moldable vacuum cushion and away from patient's body surface. This may help to reduce imaging artifacts on the target tissue during an imaging scan (e.g., a CT imaging scan) compared to the conventional approach that often includes electronic cables located on top of patient's body during an imaging scan. This may also reduce the risk of induced current during MRI scanning as the patient support device may function as a buffer layer to isolate the patient's body from long conductive cables. Since such flexible cables or printed traces may be also fixed at defined positions without making a loop or twisted with each other, this may also reduce the risk of forming a loop antenna which can generate MR imaging distortion. In addition, providing flexible cables or printed traces inside of the patient support device may make it easier to clean and disinfect the patient support device after each clinical usage.

According to an embodiment of the disclosure, the patient support device with integrated sensors could be powered by at least one main energy source that may include a battery and/or optical energy via optical cable(s) and/or contactless electromagnetic field to avoid the use of conductive metal cables which can generate MRI/CT image artifacts. In some embodiments, optical cable(s) may be used to transmit both data signals and power energy to the integrated sensors. In embodiments in which optical cable(s) are used to transmit power energy, an optical power converter may be used to convert light energy from the optical cable(s) to electric power energy.

Similarly, a processor of the system may transmit control signal(s) for operating a component of an active medical device via an optical communication channel (e.g., using optical fibres) and/or via a wireless communication channel without using conductive metal cables which can generate MRI/CT image artifacts.

According to various embodiments of the disclosure, the measured bio-impedance may be used to estimate body composition in terms of water/fat/muscle mass or percentage in a reproducible way from time-to-time during follow-up treatment sessions. Such parameters may provide clinicians a better understanding of patient body changes over time, and may also be used to determine whether original treatment planning is still valid or needs to be updated. Knowing such parameters ahead of time may also be helpful for clinicians to set optimized machine settings of an imaging device (e.g., an MRI or CT scanner) to obtain better targeted anatomy imaging quality or categorize the patient body character to certain group which is linked to pre-optimized machine setting.

According to various embodiments of the disclosure, the measured bio-impedance may also be used to analyze galvanic skin response as an indication of the patient's stress during a diagnostic imaging scan and/or during radiation treatment. If a patient shows a significant increase in stress level, it is more likely that the patient will not be still during a diagnostic imaging or treatment procedure, which can result in image artifacts and/or incorrect radiotherapy due to unexpected body motion. Such risk may be reduced as the patient's stress level may be automatically analyzed by a processor of the system, such that processor may automatically generate a control signal to de-active a medical image device and/or radiotherapy device when the patient's measured stress level is above a threshold level.

According to various embodiments of the disclosure, the measured bio-impedance from the backside of the patient may be further analyzed by a processor of the system to generate cardiac activity and/or respiration activity and/or other body motion simultaneously or at an acceptable clinical level. Unlike conventional systems that utilize a separate device on top of the patient's body to measure cardiac activity and respiration activity using complex patient setup equipment, the patient support device according to various embodiments may be a single stand-alone device and may provide various biometric data in a straightforward way. Additionally, unexpected body motion like coughing may be distinguished from regular respiration and cardiac activity such that a processor of the system may automatically de-activate an active medical device, such as a radiotherapy device during lung cancer treatment. Similarly, a large body motion, such as a patient falling, may be detected and may trigger a de-activation of the active medical device.

According to another embodiment of the present disclosure, a method of treating cardiac arrythmia includes providing a patient support device including a sensor array between a patient and a patient table, non-invasively measuring biometric data of the patient using the sensor array of the patient support device to identify cardiac and respiratory body motion states of the patient, triggering a non-invasive imaging device to obtain images of the patient's heart anatomy based on defined cardiac and respiratory motion states of the patient, generating a co-registered map of electrical activity and anatomy of the heart at the defined cardiac and respiratory body motion states, determining one or more target treatment regions of the patient's heart anatomy using the co-registered map, and directing a non-invasive therapy to the one or more target regions at the defined cardiac and respiratory body motion states. The non-invasive therapy may include, for example, stereotactic radiosurgery, stereotactic body radiotherapy, stereotactic ablative radiotherapy, fractionated radiotherapy, or hypofractionated radiotherapy.

According to an embodiment of the disclosure, a non-invasive method for imaging, planning treatment of, and treating cardiac arrhythmia may utilize an integrated sensor array to non-invasively measure electrical potentials at a plurality of locations on the subject to identify the arrhythmia and to generate a heart image including heart-torso geometry from measured electrical potentials.

According to an embodiment of the disclosure, a non-invasive method for imaging the arrhythmia or the treatment planning system further includes a peripheral for defining an arrhythmia target based on measured biometric data from patient support device and map measured biometric data with medical images such as CT/MRI scans.

According to an embodiment of the disclosure, a radiotherapy device may include a LINAC or any other suitable device capable of delivering radiation to an anatomical region of interest of a patient in a controllable and predictive manner of defined cardiac/respiration state. A processor may control the radiotherapy device according to a radiotherapy treatment plan. The treatment plan may include information about a particular dose to be applied to a particular patient, as well as other parameters such as irradiation angle, beam position, beam size, beam intensity, beam energy, dose-histogram-volume information, the number of radiation beams to be used during therapy, the dose per beam, and the like. The processor may control various components of radiotherapy device, such as chassis, beam generator, and beam shaping device, according to the treatment plan. In some embodiments, the processor may generate a treatment plan using images received from an imaging device. Alternatively or additionally, the processor may acquire a treatment plan from a database and may execute the plan with the radiotherapy device. In some embodiments, the processor may modify a treatment plan received from database prior to execution with radiotherapy device.

According to yet another embodiment of the present disclosure, a non-invasive method for determining a biological motion state inside the body of a patient includes receiving biometric data from integrated sensors of a patient support device and medical image data from medical imaging device, synchronizing the biometric data with the medical image data, and generating at least one artificial signal that represents a predicted biological motion state inside the body of the patient using the synchronized biometric data and medical imaging data.

In some embodiments, the predicted biological motion state may be identified based on a principal component analysis. In some embodiments, the artificial signal may be generated using a machine learning process, such as an empirical learned model that combines features from a set of features with respective learned weights, and/or a regression function that is trained using image-based boosting ridge regression. In various embodiments, the method may further include controlling an operation of a medical device based on the artificial signal when a confidence level of the predicted biological motion state is above a threshold level.

Other and further aspects and features will be evident from reading the following detailed description of the embodiments, which are intended to illustrate, not limit, the invention.

DETAILED DESCRIPTION

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Medical imaging is commonly used to assist in the diagnosis and/or treatment of patients. X-Ray imaging is an example of a medical imaging technology that is often performed during the diagnosis and/or treatment of tumors. The treatment of tumors may be performed by using ionizing radiation provided by a linear accelerator (LINAC) generating a radiation beam of electrons and/or protons having particular energies. In such a radiotherapy system, the radiation beam should be aimed as precisely as possible at the target volume or target tissue, namely the tumor, while the adjacent healthy tissue should as far as possible not be irradiated. An embodiment radiotherapy system may include a couch for supporting the patient to be diagnosed and/or treated. An embodiment system may further include a gantry which may be configured to be rotatable around a gantry axis and having and/or carrying a radiation source. In particular, the gantry may be moved to different positions in the circular orbit to deliver a radiation beam from these positions to a target volume of the patient. The radiation source may comprise and/or may be referred to as a radiation head, a collimator, such as a multi-leaf-collimator (MLC), etc. In this context, the gantry itself may also be considered as the radiation source. An embodiment system may also include at least one radiation imaging device. The radiation imaging device may be provided as a kilo-electron-volts (keV) and/or mega-electron-volts (MeV) imaging device configured to provide 2D, 3D and/or 4D imaging.

Figure 1:
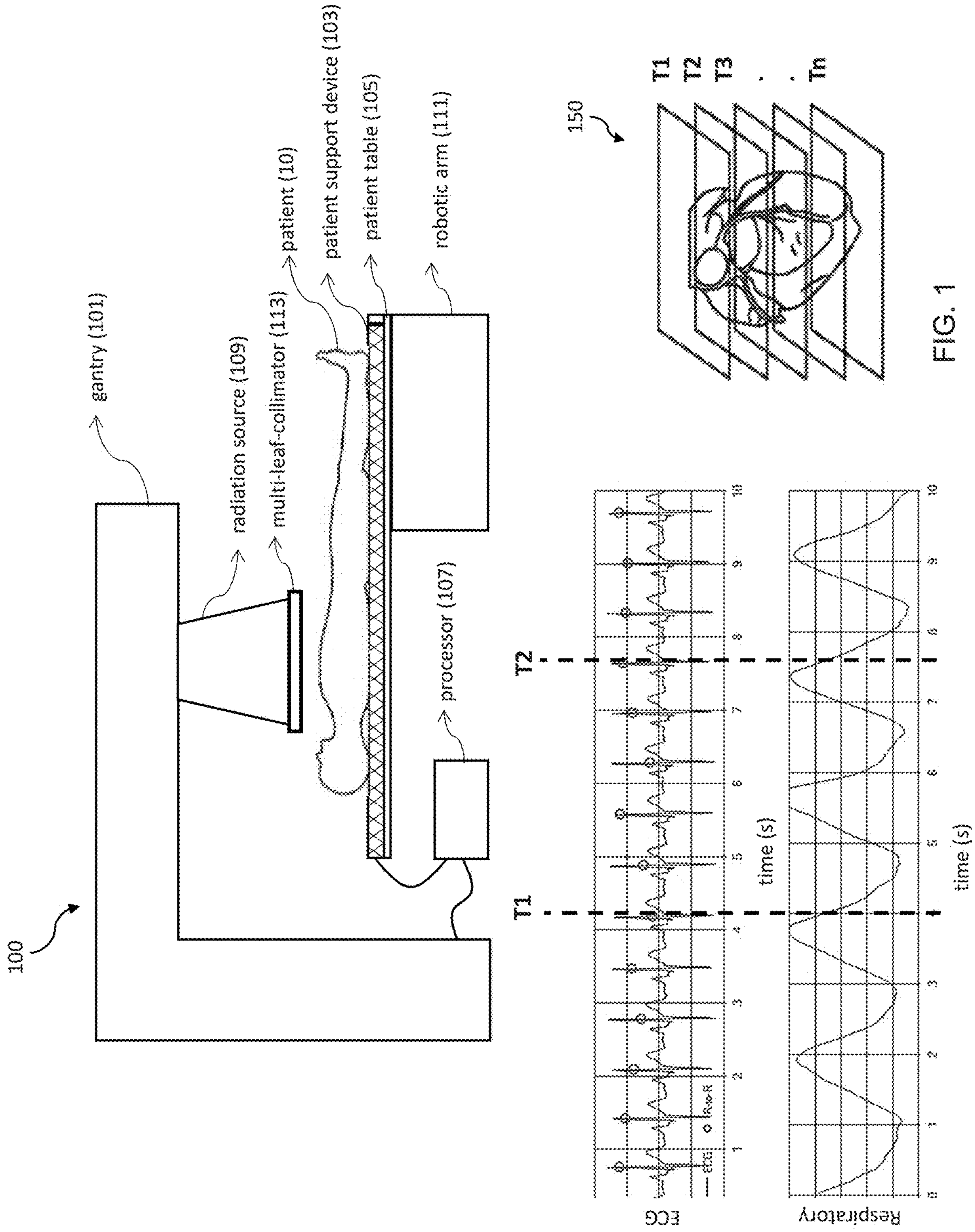
FIG. 1 illustrates a radiation system in accordance with some embodiments.

FIG. 1 illustrates a radiation system 100 in accordance with various embodiments of the present disclosure. The radiation system 100 shown in FIG. 1 is a treatment system that includes a gantry 101, a patient support device 103 disposed between a patient 10 and a patient table 105, and a processor 107 for controlling the operation of the radiation system 100. A table support 111, which may include one or more robotic arms, may support the patient table 105 and may move the patient table 105 (which may also be referred to as a "treatment table" or a "couch top") to a desired position. The gantry 101 may be in the form of a c-arm that may rotate with respect to the patient table 105, the patient support device 103, and the patient 10. The radiation system 100 also includes a radiation source 109 that is operable to project a beam of radiation towards the patient 10 while the patient is supported on patient support device 103, and a multi-leaf-collimator system 113 for controlling a delivery of the radiation beam. The radiation source 109 may be configured to generate a cone beam, a fan beam, or other types of radiation beams in different embodiments.

In the illustrated embodiments, the radiation source 109 is a treatment radiation source for providing treatment energy. In other embodiments, in addition to being a treatment radiation source, the radiation source 109 may also be a diagnostic radiation source for providing diagnostic energy for imaging purposes. In such cases, the system 100 may include a radiation detector, which may also be referred to as an imager (not shown), that may be located at an operative position relative to the source 109. Alternatively or additionally, a separate radiation source and detector may be used for obtaining diagnostic images of the patient 10. In some embodiments, a separate radiation source and a radiation detector/imager for obtaining diagnostic images may be mounted to the gantry 101. In some embodiments, the energy of the treatment radiation from the radiation source 109 may be 150 keV or greater, and more typically 1 MeV or greater. The energy of the radiation used for diagnostic imaging may be below the energy range of the treatment radiation, and may be below about 150 keV. In other embodiments, the treatment energy and the diagnostic energy can have other energy levels, and refer to energies that are used for treatment and diagnostic purposes, respectively. In some embodiments, the radiation source 109 is able to generate X-ray radiation at a plurality of photon energy levels within a range anywhere between approximately 10 keV and approximately 20 MeV. In further embodiments, the radiation source 109 may be a diagnostic radiation source. In the illustrated embodiments, the radiation source 109 is coupled to the gantry 101.

It should be noted that the system 100 is not limited to providing treatment radiation in the form of X-rays, and that the system 100 may be configured to provide other form of treatment radiation. For example, in other embodiments, the radiation source 109 of the system 100 may be configured to provide radiation having electrons, positrons, neutrons, protons or other particles.

It should be also noted that the system 100 may include radiation source and an alternative medical imaging device. For example, the radiation system 100 may be a combination magnetic resonance imaging (MRI) and linear accelerator system, known as an MR-LINAC. Accordingly, the radiotherapy device may be a LINAC device, and the medical imaging device may be an MRI device. The imaging device may provide medical images of a patient. For example, the imaging device may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, the imaging device may include an MRI imaging device, a CT imaging device, a PET imaging device, an ultrasound imaging device, a fluoroscopic device, a SPECT imaging device, or other medical imaging devices for obtaining the medical images of the patient 10. The imaging device may be configured to acquire one or more images of the patient's anatomy for a region of interest (e.g., a target organ, a target tumor or both). Each image, typically a 2D or 3D image slice, can include one or more parameters (e.g., a slice thickness or volume, an orientation, and a location, etc.). FIG. 1 illustrates an example of a medical image 150, which in this example is an image of a patient's heart. The medical image 150 may be a 3D volumetric image data set. A display device (not shown) may be configured display a 3D volume rendering of the patient's anatomy and/or 2D cross-sectional images (i.e., image slices) of the patient's anatomy along one or more desired planes (e.g., T1, T2, T3 . . . Tn). In an example, the imaging device may acquire and/or display an image slice in any orientation. For example, an orientation of the image slice can include a sagittal orientation, a coronal orientation, or an axial orientation. A controller, which may be processor 107 or a separate processing device, may adjust one or more parameters, such as the size and/or orientation of the image slice, to include the target organ and/or target tumor. In an example, image slices can be determined from information such as a 3D MRI volume. Such image slices may be acquired by the imaging device in "real-time" while a patient is undergoing radiation therapy treatment, for example, when using radiotherapy device.

A radiation system 100 such as shown in FIG. 1 may also include one or more sensors for measuring various biometric parameter(s) of the patient 10, such as parameters relating to cardiac and/or respiratory activity of the patient 10. The biometric parameters may be recorded in a suitable storage medium and/or displayed in "real time" on a suitable display device. FIG. 1 illustrates an example of a real-time display of biometric parameters, which may include electrocardiogram (ECG) measurements and/or respiratory activity measurements. In various embodiments described in further detail below, the one or more sensors for measuring biometric parameters, such as bio-impedance parameters, may be located in the patient support device 103, and may be operatively coupled to processor 107.

Figure 2:
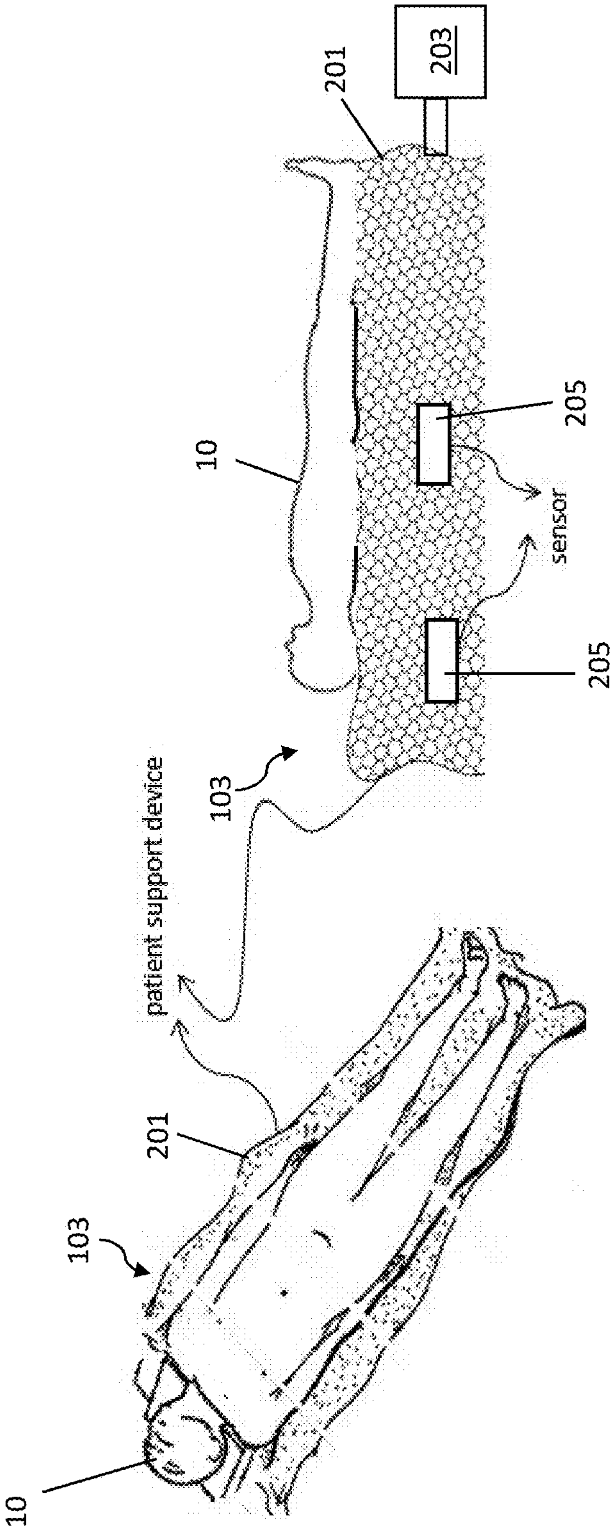
FIG. 2 illustrates a patient support device in accordance with some embodiments.

FIG. 2 illustrates a patient support device 103 in accordance with some embodiments. A top perspective view of a patient 10 on the patient support device 103 is shown on the left-hand side of FIG. 2, and a vertical cross-section view of the patient 10 on the patient support device 103 is shown on the right-hand side of FIG. 2. In various embodiments, the patient support device 103 may be composed of a soft material which provides certain comfort to the patient. In addition, or alternatively, the patient support device 103 may include a moldable vacuum cushion 201 comprising a flexible bag of gas-impermeable material; a flowable filling material such as polystyrene grains or balls; and a valve to allow the bag to be connected to an external vacuum source or a vacuum pump 203. The vacuum cushion 201 may include one or more sensors 205. The one or more sensors 205 may include one or more of an accelerometer, a gyroscope, an inclinometer, a photoplethysmogram, or another similar sensor that is configured to provide physic of patient's motion parameters. The one or more sensors 205 may also measure a bio-impedance parameter of the patient 10 to reveal internal organ activities such as cardiac motion, lung motions, or the like.

The vacuum cushion 201 may also include at least one bolster (not shown). For example, the bolster can be shaped to locate a shoulder region of the patient in a comfortable, reproducible position for each treatment fraction; or support the knees of the patient in an elevated position; or be a substantially cylindrical neck roll to support underneath a neck of the patient. The use of additional bolsters or cushions may reduce patient movement; improve patient comfort and provide better beam access for treatment. The patient support device 103 may be placed on a patient table 105 as shown in FIG. 1, and may be fixed thereto; for example at successive indexed fixing points along the patient table 105. The patient table 105 and patient support device 103 may be releasably fixed together; for example, using a releasable, elongated bar with two pins projecting to be received in corresponding holes in the patient support device 103; or the patient support device 103 may be releasably fixed to the patient table 105 using a hook and loop fastener or similar attachment mechanism.

In various embodiments, the vacuum cushion 201 may be made from a flexible material and may be formed as a vacuumable cushion having a variable shape or volume that may change due to the air operation. Accordingly, the shape or volume of the vacuum cushion 201 may change as the inner volume of the cushion is evacuated by the air pumping device 203. A material suitable for the patient support device 103 may be air or gas tight, impermeable and/or may have insulating properties, such as foam, expanded polypropylene foam, polyurethane foam, polyamide foam, polyether ether ketone (PEEK) foam and biocompatible surface foam based on EVA (ethylene-vinyl acetate). Those exemplary materials are non-conductive and transparent to the medical imaging device like CT and/or MRI such that it will not generate unacceptable image artifacts which could result in an incorrect diagnosis or incorrect treatment planning. In various embodiments, a patient support device 103 including vacuum cushion 201 may be molded to the patient's anatomy and may allow the patient to be positioned in the same position for medical imaging and treatment, including during subsequent imaging or treatment sessions. In some embodiments, the patient support device 103 may include fiducial markers which may be visible in an X-ray image or in an MR image together with the patent's anatomy images. Once the fiducial markers are registered with patent's anatomy images, this may allow clinicians to determine the spatial position and orientation of the patent's anatomy based on the images from fiducial markers.

Figure 3A:
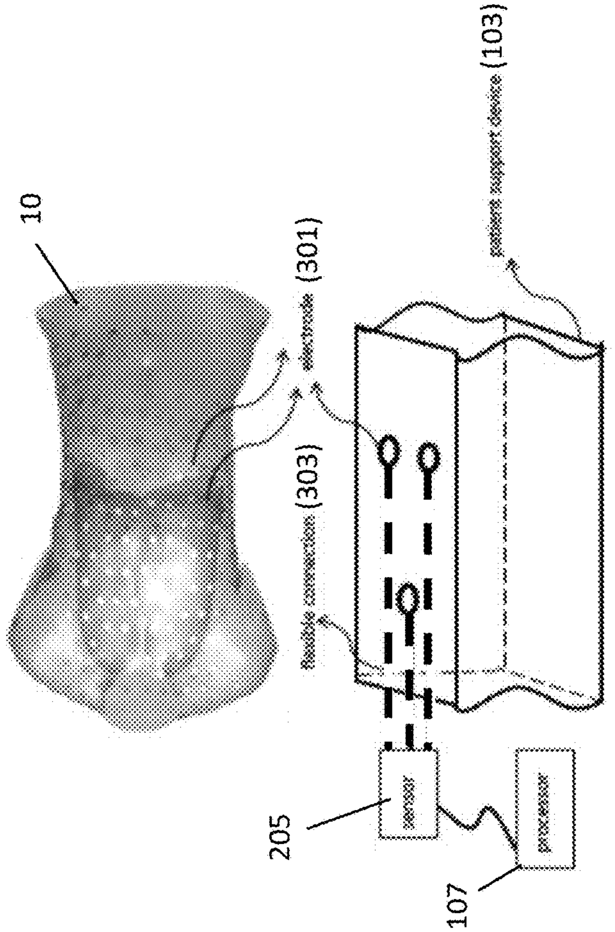
FIGS. 3A and 3B illustrate patient support devices with integrated skin-electrode interfaces in accordance with some embodiments.
Figure 3B:
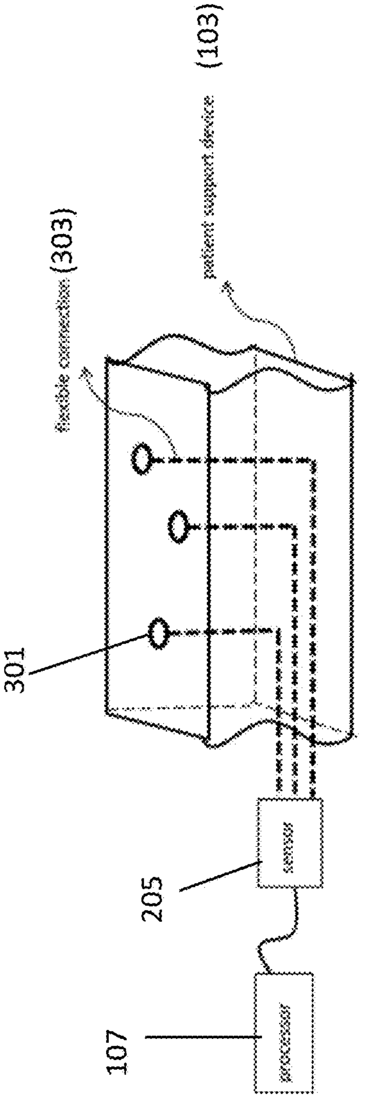

FIGS. 3A and 3B illustrate patient support devices 103 with integrated sensors 205 to measure bio-impedance parameters of patient to reveal internal organ activities such as cardiac motion, lung motions, or the like. In particular, a patient support device may include a skin-electrode interface array. The skin-electrode interface array may include a plurality of electrodes 301 located at pre-defined positions for measuring multiple electronic potentials/bio-impedances across the patient's body. FIG. 3A shows a perspective view of a torso of a patient 10 illustrating the locations of electrodes 301 with respect to the patient's body when the patient 10 is located on the patient support device 13. Since a patient support device 103 including a vacuum cushion 201 may be molded to the patient's outline shape and may allow the patient to be repeatedly positioned in the same position, the readout of measured bio-impedance may be highly reproducible. This is in contrast to the conventional technique that includes manually attaching electrodes at estimated body positions, which is a time-consuming process and is generally non-reproducible. As shown in FIGS. 3A and 3B, a plurality of interconnections 303 may couple each of the electrodes 301 of the array to a sensor 205 that may be configured to measure a bio-impedance parameter of the patient 10 based on signals received from the electrodes 301. The sensor 205 may be operatively coupled to a processor, such as processor 107 shown in FIG. 1.

FIG. 3A illustrates the interconnections 303 between each skin-electrode interface and the sensor 205 including 2D printed conductive signal traces, which may be located on the backside of cover surface of the patient support device 103. FIG. 3B illustrates the interconnections 303 between each skin-electrode interface and the sensor 205 including flexible and stretchable PCB/cables located inside of the patient support device 103. In various embodiments, interconnections 303 that are in the form of flexible cables or printed traces may be deformed with the deformation of a moldable vacuum cushion and away from patient's body surface. This may reduce the imaging artifacts on the target tissue during CT scanning compared with the conventional approach that typically includes putting electronic cables on top of the patient's body. This may also reduce the risk of induced current during MRI scanning as the patient support device 103 may function as buffer layer to isolate the patient's body from long conductive cables. Since interconnections 303 in the form of flexible cables or printed traces may also be fixed at defined positions without making a loop or becoming twisted with each other, this may reduce the risk of forming a loop antenna which often generates MR imaging distortion. In addition, providing interconnections 303 in the form of flexible cables or printed traces inside of the patient support device 103 may make it easier to clean and disinfect the patient support device 103 after each clinical usage.

The electrodes 301 may be of any suitable type such as wet-contact gel-based Ag/AgCl, dry-contact microelectromechanical systems (MEMS) and metal plate, thin-film insulated metal plate, flexible as well as stretchable electrode. Generally, non-invasive body surface electrodes can be divided into three categories: wet, dry contact, and dry noncontact. Typical wet electrodes with Ag/AgCl and hydrogel ensure an easy conversion between ionic current and electron current, resulting in low electrode impedance up to a few kilohms. Dry contact electrodes eliminate the use of gel, at the cost a higher impedance ranging from several hundreds of kilohms up to a few tens of megohms. Dry noncontact electrodes isolate the electrode and skin by capacitive coupling, but this leads to even higher electrode impedance and increased susceptibility to motion artifacts. The impedance of dry noncontact electrodes mainly depends on garment hair, the distance of air gap and the surface area of electrodes. In recent years, some new electrode concepts have been proposed to reduce the electrode impedance, such as quasi-dry electrodes, a concept between "wet" and "dry" electrodes. These electrodes hydrate the local skin area by releasing a small amount of moisturizing solution from the electrode reservoir, and achieve impedance in the order of a few tens of kilohms. Polarization voltage, or half-cell potential, develops across the electrolyte-electrode interface because of the unbalanced distribution of anions and cations while electrode offset is the differential polarization voltage between electrodes, and it depends on the electrochemical unbalance of two electrodes, i.e., materials, temperature, and the ion concentration of body fluid; Ag/AgCl electrodes are widely used due to its low polarization. Regarding user comfort, dry electrodes implemented with conductive metal contact with patient's skin can provide long-term stable recording but at the cost of discomfort and pain. Alternative electrodes like silver-coated polymer bristles, dry foam electrodes, polymer electrodes made of polydimethylsiloxane or polyurethane, and comb-shaped polymer electrodes can provide soft contact to the skin while still providing low electrode impedance. The wearable dry electrodes can also be realized by embedding conductive nanomaterials, such as Agnanowire, carbon nanoparticles, Ag-coated glass composites, and carbon nanotubes (CNT), in the flexible polymers or by employing a coating of conductive material, such as Ni, Cu, and Au, on the polymer substrate. The electrode can be a self-adhesive, stretchable platinum silicone rubber-based substrate to estimate and minimize the electrode displacement through an adaptive filtering approach. These dry wearable electrodes are suitable for long-term monitoring of cardiac, respiration and other kinds of body motions.

It should be noted, that the electrodes may contain fiducial markers which are visible in an X-ray images or an MR-image together with the patent's anatomy images. Once the fiducial markers are registered with patent's anatomy images, this may allow clinicians to determine the spatial position and orientation of the patent's anatomy based on the images from the fiducial markers.

The patient support device 103 with integrated sensors 301 may be powered by at least one energy source including a battery and/or optical energy via optical cables and/or contactless electromagnetic field to avoid use conductive metal cables which can generate MRI and CT image artifacts.

In some embodiments, optical cable(s) may be used to transmit both data signals and power energy to the integrated sensors 301. In embodiments in which optical cable(s) are used to transmit power energy, an optical power converter may be used to convert light energy from the optical cable(s) to electric power energy.

Similarly, the processor 107 may transmit a control signal to control the operation of a component of an active medical device via an optical communication channel, such as an optical fibre-based communication channel and/or via a wireless communication channel without using conductive metal cables which can generate MRI/CT image artifacts.

In various embodiments, the sensor(s) 205 of the patient support device 103 may measure bio-impedance of the patient 10 non-invasively and in real time to determine internal organ motions like cardiac activity and respiration activity. In various embodiments, a method for determining body impedance may be based on applying an electrical potential difference between the electrodes 301 of the patient support device 103 and measuring a resulting electrical current passed between the electrodes 301. In some applications, the electrodes 301 may be reproducibly placed at the treatment areas or other target volume on marked locations on the patient such that the same electrode positions may be used to obtain bio-impedance signals for each of a plurality of treatment and/or imaging applications. In human tissue, the application of an alternating current results in an impedance profile that correlates with frequency. Living tissue consists of intra- and extracellular space which acts as an ionic conductor and cellular membranes that have the property of an electrical insulator. At low frequencies (≤1 kHz) the current is mainly carried by the extra-cellular fluid, while at higher frequencies (≥500 kHz) the current passes through the intra- and extracellular compartment. Tissues are considered to be volume conductors that have continuous distribution of electrical properties. Due to anisotropy, the electrical properties may vary significantly in different directions. The human thorax can be modelled as a finite piecewise homogenous volume conductor, in which organs are modelled as homogenous volume conductors. Importantly, the electrical properties of the thorax vary in time due to changes in blood volume and flow following the cardiac cycle as well as the respired air following the respiratory state.

Figure 4:
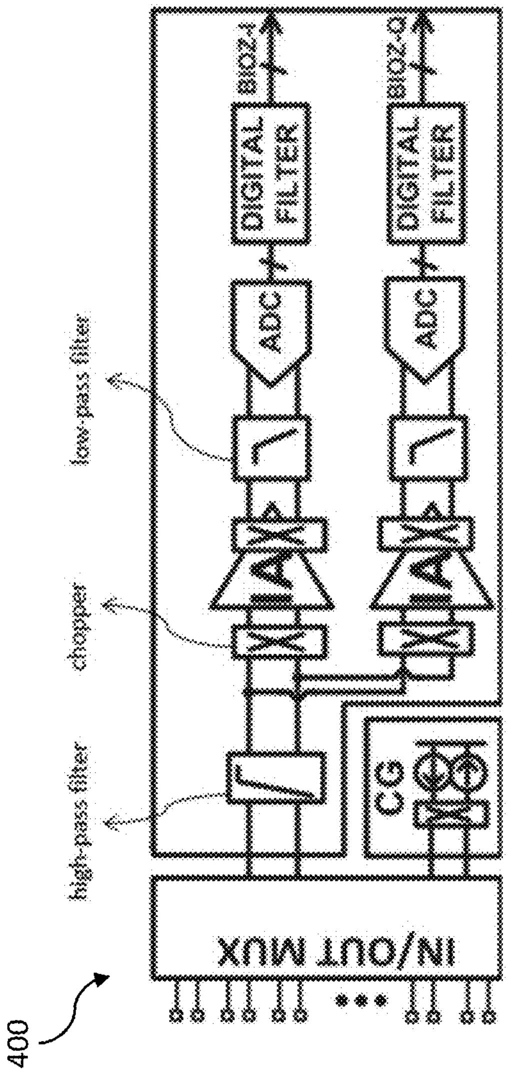
FIG. 4 is a conceptual block diagram of a bio-impedance sensor in accordance with some embodiments.

FIG. 4 illustrates a conceptual block diagram of bio-impedance sensor 400 that may be used to concurrently measure cardiac activity, respiration activity and/or other motion activity. The bio-impedance readout channel in this example has a fully integrated high pass filter (HPF) at its input followed by a chopper-modulated instrumentation amplifier (IA). This allows concurrent measurement of in— (I) and quadrature-phase (Q) outputs. The programmable in/out multiplexer (MUX) allows a configurable connection to up to 256 electrodes. The digital logic specifies, in a programmed sequence order, the connections to electrodes and generates the current injection clock with a frequency (f_clock) configured between 1 kHz to 10 MHz. The current generator (CG) supplies a differential square wave current of at f_clock. The current is firstly generated in DC (I_out) by 1: N programmable current mirrors and modulated to f_clock. The flicker noise of the I_out is also modulated to f_clock and is often the dominant noise source in bio-impedance recordings. The readout amplifies each modulated voltage at f_clock across the tissue impedance. Pre-demodulation to an intermediate chopper frequency in front of the IA is adopted. The input signal at f_clock is first demodulated to DC and modulated to chopper frequency before where the signal will be amplified by IA. Therefore, a wide frequency range of bio-impedance measurements may be implemented with a narrow-BW (<100 kHz) low-power IA and the flicker noise mitigation may be preserved by means of chopping.

Figure 5:
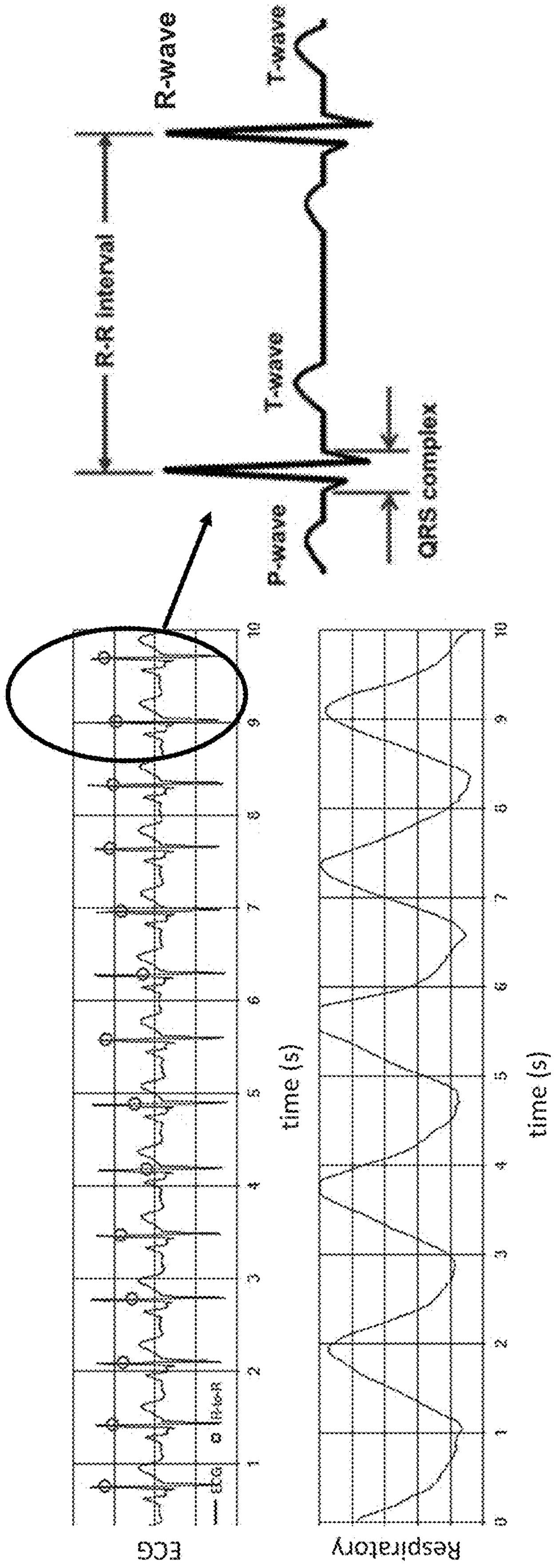
FIG. 5 illustrates concurrent cardiac activity and respiration activity measurement from bio-impedance sensors according to various embodiments.

FIG. 5 illustrates measured cardiac and respiration activity from bio-impedance sensor, such as the bio-impedance sensor 400 shown in FIG. 4. The bio-impedance sensor 400 may be integrated with a patient support device 103 such as shown in FIGS. 1-3B. Cardiac activity such as electrocardiographic (ECG) measurements may be monitored based on the measurement of varying impedance due to changes in blood volume and flow in the thorax following cardiac contraction. Blood has low impedivity in contrast to other tissues; thus, an increased amount of blood in the thorax following the systole can be detected as a decrease of the impedance of the thorax. The measured results can be used in non-invasive detection of stroke volume, cardiac contractility, diastolic dysfunction, arrhythmias and systolic time intervals, for example.

Respiration may be simultaneously monitored based on transthoracic bio-impedance measurements. The measurement reflects the varying lung air content. In addition, everything that has an effect on the current pathways in the thorax during respiration, that is, the change in thorax shape and organ motion, affects impedance measurement. The measured impedance includes apnea detection and respiratory flow measurements as well as monitoring of intrathoracic fluid accumulations such as lung oedema. Conventionally, cardiac activity and respiratory activity is measured using a separate device that is positioned on top of the patient's body, which often requires a complex set-up of the measurement equipment on the patient. In contrast, various embodiments of the present disclosure may provide a patient support device 103 with integrated biometric sensors, including bio-impedance sensors, in a stand-alone device that may provide various biometric data in a straightforward way. Additionally, unexpected body motion like coughing may be distinguished from regular respiration and cardiac activity such that a processor 107 operatively coupled to the patient support device 103 may be configured to automatically de-activate a medical device, such as a radiotherapy device or an imaging device, during a treatment or imaging procedure, in response to an unexpected body motion.

Another application of bio-impedance measurements is to estimate body composition in terms of total body water (TBW)/fat mass (FM)/fat-free mass (FFM) or percentage in a reproducible way from time-to-time during follow-up treatment sessions. Such parameters may provide clinicians with a better understanding of patient body change over time, which may aid in determining whether an original treatment plan is still valid or requires updating. Knowing such parameters ahead of time may also be helpful for clinicians to set optimized machine settings of imaging devices, such as MRI or CT scanners, in order to obtain better targeted anatomy imaging quality or to categorize the patient body character to a certain group which is linked to a pre-optimized machine setting. Compared with other techniques with require expensive equipment and time-consuming measurement processes, such as hydro densitometry, air displacement plethysmography and dual-energy X-ray absorptiometry (DXA), magnetic resonance imaging (MRI) and computed tomography (CT), the present approach is straightforward as the bio-impedance sensors may be integrated as part of a patient support device 103 without requiring extra manual effort for patient setup.

Patient body composition may be estimated based on measuring the resistance and reactance of an alternating electrical current in the human body using bio-impedance sensors integrated in the patient support device 103. Intracellular fluids, body fluids and electrolytes behave as electrical conductors (resistance), and cell membranes act as electrical capacitors and are involved in capacitance (reactance). Body fluid is the total volume of fluids inside a human body that represents the majority of the FFM volume percentage.

The measured raw impedance may be measured at various frequencies and further interpreted by empirical model(s) to estimate fat mass (FM), fat-free mass (FFM), and total body water (TBW). For example:

$$FFM=-4.104+0.518*H*H/R+0.231*W+0.13*X+4.229*S$$

$$FM=14.94-0.079H*H/R+0.818*W-0.231*H-0.064*S*W+0.077A$$

$$TBW\ (male)=1.2+0.45H*H/R+0.18*W$$

$$TBW\ (female)=3.75+0.45H*H/R+0.11*W$$

where H is body height, R and X is resistance and reactance at 50 KHz, W is body weight, A is age, and S equals 1 for male and 0 for female. These personalized parameters may also be used for patient identification.

Another application of bio-impedance measurements may be to analyze galvanic skin response as an indication of the patient's stress during a diagnostic imaging scan or during radiation treatment. In embodiments in which a patient shows a significant increase in stress level, it may be more likely that the patient will not be able to remain still, which may result in image artifacts or incorrect radiotherapy due to unexpected body motion. Such risk may be reduced by using the processor to analyze the patient's galvanic skin response, such that the processor may automatically generate a control signal to de-active the medical image device or radiotherapy device when the measured galvanic skin response indicates an excessively high patient stress level.

Cardiovascular diseases are the leading cause of mortality worldwide and represent a huge health and economic burden. Ventricular tachycardia (VT) is the most life-threatening arrhythmia. It is responsible for over 80% of sudden cardiac death. Cardiac arrhythmia is any alteration in the heart's electrical system that prevents it from beating properly. Cardiac arrhythmia may cause the heart to beat too fast (tachycardia), too slow (bradycardia), or in any other irregular pattern. These abnormalities can influence the blood quality that is supplied to the rest of the body, or even prevent it from flowing through the rest of the body. Device-based therapies, involving the use of implantable cardioverter-defibrillators (ICDs), are indicated for prevention of sudden cardiac death in patients with a structural disease. However, the implantation of such devices is expensive and non-curative. It requires the devices to be surgically implanted in the chest where the devices may deliver precisely calibrated electrical shocks when needed to restore normal heart rhythm. Catheter ablation of the ventricular arrhythmogenic substrate has been proven to be an alternative treatment for VT. It consists of inserting a long thin wire through the veins of the leg and targeting the site of the origin of the VT. The site of origin is then eliminated by radiofrequency, laser, thermal or ultrasound energy. This catheter ablation method has many risks of invasive nature of introducing several catheters into the heart and failure could lead to fatal error.

Various embodiments of the present disclosure include non-invasive imaging of an arrhythmia and a non-invasive treatment method of cardiac arrhythmia. Various embodiments include methods of treating cardiac arrhythmia that may include computing heart electrical activity data from a set of non-invasively measured body surface electrical potentials from a patient support device 103 as previously described, and/or using a separate device; obtaining a patient's heart-torso geometry using a non-invasive imaging device; providing a patient support device 103 including an integrated sensor array under the patient's body and using the patient support device 103 to non-invasively measure biometric data of the patient to identify cardiac, respiration and other body motions simultaneously; trigging a non-invasive imaging device to obtain images of the patient's heart anatomy based on defined cardiac and respiration states; generating a co-registered map of the heart's electrical activity and the heart's anatomy at the defined cardiac and respiration states; determining one or more target treatment regions using the co-registered map; optionally repositioning the patient (e.g., from a radiology room to a radiotherapy treatment room); and directing a non-invasive therapy, such as radiation therapy, to the one or more target regions at the defined cardiac and respiration states.

In one aspect, the disclosed methods and systems can be implemented using a processor configured to allow the user to define the arrhythmia target using ECGi data overlaid on an anatomy image set (e.g., a CT and/or MR image set) of a patient's torso and then translate the defined target on the image set back into image set slices that can may be imported into a treatment planning system (TPS). These images can subsequently be co-registered to the primary planning image dataset per standard treatment planning, and may be used to define the arrhythmia target on the primary planning image dataset.

It will be understood that there are many methods for obtaining non-invasive images of a heart and an arrhythmia such as using a magnetic resonance imaging (MRI) device, an X-ray device, a computed tomography (CT) device, a cardiac ultrasonography device, a positron emission tomography (PET) device, an ElectroCardioGraphic imaging (ECGi) device, etc. In one aspect, the disclosed systems and methods may utilize a non-invasive imaging means including ECGi and/or anatomic imaging devices (where the electrical and anatomic character of arrhythmia may be determined without the need to map the actual arrhythmia). As used herein, "electrocardiographic imaging" (ECGi) refers to a technique which reconstructs epicardial potentials, electrograms, and activation sequences (isochrones) from electrocardiographic body-surface potentials noninvasively.

Conventional approaches often require the patient to undergo a CT scan while wearing a vest of electrodes that records electrical activity. The major electrical activity signal is from cardiac electrical activity. The electrical potentials/bio-impedance from the surface of the body may then be registered to a patient-specific heart model derived from the CT images to display the characteristics of the cardiac electrical activity mapped onto a patient's heart anatomy. Useful information includes: where the heart beat begins, the depolarization sequence of the heart tissue, and which parts of the heart have abnormal depolarization behaviour. There are several techniques that may be used to solve the electrocardiographic inverse problem, which due to computation of epicardial potentials from body surface potentials can often result in significant errors. Regularization methods (typically Tikhonov regularization or the generalized minimal residual method) may be used to minimize error. Typically, ECGi includes electrocardiographic unipolar potentials measured over the entire body surface and the heart-torso geometrical relationship. In one aspect, ECGi can utilize a vest with multiple electrodes strapped to the subject's torso and connected to a multichannel mapping system for measuring electrical potentials over the body surface. ECGi incorporates the patient-specific anatomy of the heart with the recording leads on the body surface to noninvasively reconstruct the electrical activity on a three-dimensional model of the patient's heart surface. As used herein ECGi is understood to include other iterations that use mathematical solutions for the inverse problem of electrocardiography, which uses electrical potentials measured at the body surface and reconstructs them onto a model of the surface of the heart. In general, such processes are very time consuming and not reproducible due to the patient's motion, including respiration or unexpected motion (e.g., coughing) during the measurement which can displace electrode positions and yield incorrect ECGi as well as motion related CT imaging artifacts. Moreover, such patient motion also introduces additional difficulties in co-registering ECGi data and images of patient's anatomy, which may be based on CT images. Similarly, the patient typically needs to be repositioned from a radiology room to a treatment room, which can generate extra positioning errors due to an inability to accurately reproduce the patient's pose and position. In order to compensate for such positioning errors, a complex planning target volume (PTV) may be utilized that includes a volumetric expansion of the internal target volume (ITV) by 3-5 mm in all directions to account for any residual uncertainties in patient setup, motion, and delivery. This means that more healthy tissues will also be damaged due to the expended treatment volume during radiation treatment.

Figure 6:
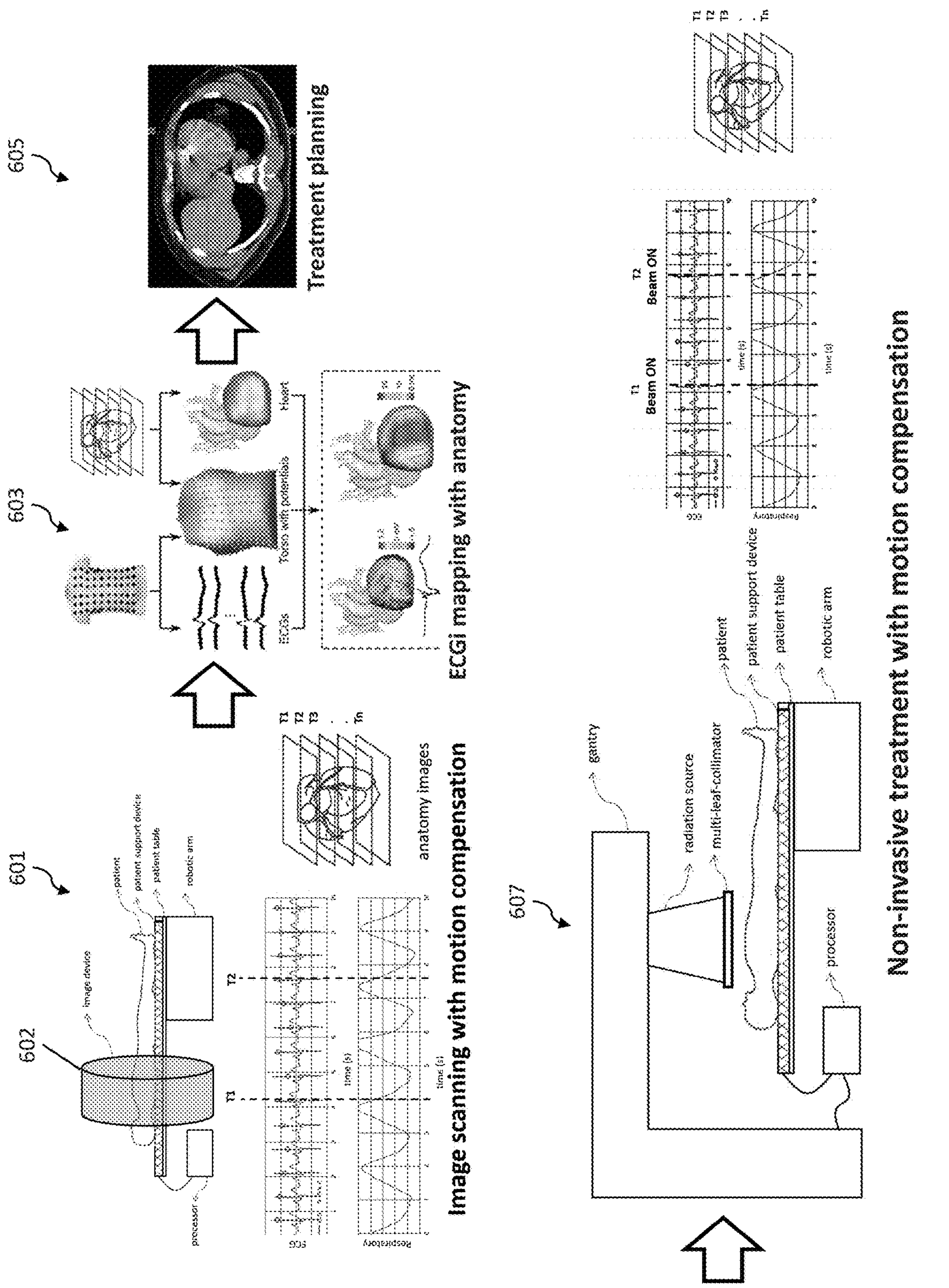
FIG. 6 illustrates a non-invasive imaging and treatment workflow for treating cardiac arrhythmias according to various embodiments.

FIG. 6 illustrates a non-invasive imaging and treatment workflow for cardiac arrhythmias according to various embodiments of the present disclosure. The workflow includes an anatomic imaging process 601 that includes obtaining an image of the target anatomy of the patient 10 (e.g., the patient's heart) using a medical imaging device 602 (e.g., a CT or MRI scanner) while the patient 10 is positioned on a patient support device 103 including integrated sensors for measuring biometric data of the patient 10. Unlike conventional techniques that use separate procedures to obtain anatomy images and ECGi which may be inaccurate due to the risks of uncontrollable body motion states (e.g., respiration, coughing), various embodiments of the present disclosure may significantly improve the image quality by simultaneously motioning cardiac/respiration activity and defining a reproducible motion state to trigger non-invasive imaging devices (e.g., CT/MRI scanner) to obtain each anatomy imaging slice at a defined body motion state in order to re-construct a 3D anatomy model without motion related artifacts. In practice, there may be a time delay between actual cardiac/respiration body motion state and the starting time of image scanning. As long as the actual cardiac/respiration body motion state is periodically reproducible, such time delay may be constant and may be compensated for by the processor 107 by adding an extra time shift to synchronize the defined cardiac/respiration motion state with the starting time of image scanning. Unlike expensive and complex conventional approaches that include performing multiple image scans within a short period and then pick up a preferred image based on a desired cardiac/respiration state, various embodiments of the present disclosure may offer a precise timeline prediction for a periodic cardiac/respiration body motion state and to trigger the image scan to coincide with the defined cardiac/respiration body motion state. In the embodiment shown in FIG. 6, for example, the patient may be in a desired cardiac/respiration boy motion state at times T1 and T2, as shown on the ECG and respiratory activity measurements. The periodicity of the defined cardiac/respiration body motion state may be determined by the processor 107 based on biometric (e.g., bio-impedance) measurements that may be obtained using sensors integrated in the patient support device 103. The processor 107 may generate control signals to control the operation of the imaging device 602 to obtain images while the patient 10 in the desired cardiac/respiration body motion state.

The workflow may also include an EGCi mapping process 603 that includes obtaining ECGi measurements of the patient, which may occur prior to, after, or simultaneously with the anatomic imaging process 601, and mapping the ECGi data onto the obtained patient anatomy images to reconstruct the electrical activity on a three-dimensional model of the patient's heart surface. Various embodiments may improve the accuracy of the ECGi mapping with the obtained anatomy images to provide an accurate heart-torso geometrical relationship. For example, such defined cardiac/respiratory motion state could be ECG R-wave at peak inhalation where lung volume is maximum as illustrated at T1 or T2 time. In practice, the patient may perform free breathing or apply active breathing control. An active breathing control device or deep inspiration breath-hold (DIBH) device may be used, which includes a mouth piece and an airflow valve which is periodically closed at a certain point in the patient's respiratory cycle to prevent airflow to and from the patient. With airflow blocked, the lungs and diaphragm may be immobilized in a reproducible way to obtain a clear anatomy image. After that, the airflow valve may be opened and respiration resumes.

Unlike in certain prior art techniques where the patient is required to wear a separate vest with multiple electrodes such that it can cover both front and back sides of the body to record electrical potentials/bio-impedance over the body surface, a patient support device 103 according to various embodiments may include an integrated electrode array to directly measure the electrical potentials from a patient's backside. Thus, in some embodiments, the ECCi procedure may only require a vest or other suitable apparatus containing electrodes provided over the front side of the patient such that patient may maintain a supine pose during the CT/MR image scan without changing pose or undressing a vest. The patient support device 103 may also include a vacuum cushion that is molded to the patient's outline shape and allows the patient to be positioned in the same position. Such vacuum cushion may also be extended or separated with more electrodes to cover the front side of the patient. In this way, the patient support device 103 with electrodes may cover both front and back sides of the body and provide the same electrical potentials/bio-impedance measurements as using a separate vest. The overall results may be more precise than conventional approaches because the ECGi mapping may be obtained and well synchronized with an anatomy image scan while the patient is in the same pose using a motion management scheme according to the present disclosure. The resulting treatment planning process 605 may also be improved because of improved CT/MR imaging quality with less motion artifacts. Similarly, the body motion detection may also applied during a subsequent treatment process 607, such as a non-invasive radiation therapy treatment process, such that the radiation beam could be trigged at the same defined cardiac/respiration body motion state (e.g., T1 and T2) as when the image scan was obtained, as schematically illustrated in FIG. 6. Any unexpected body motion (e.g., cough) may cause the processor 107 to generate a control signal to automatically disable the radiation beam and lead to a fail-safe status. In practice, there may be a time delay between the actual cardiac/respiration motion state and the actual radiation beam delivery time. As long as the actual cardiac/respiration motion state is periodically reproducible, such time delay is constant and may be compensated for by the processor 107 by adding an extra time shift to synchronize the pre-defined cardiac/respiration body motion state and the starting time of the radiation beam delivery. Various embodiments of the present disclosure may offer a precise timeline prediction for a periodically repeating cardiac/respiration body motion state and may trigger a radiation beam delivery or an additional X-ray/MR scan for verification or on-line treatment adaption in terms of changing radiation beam shape and dosage. According to an embodiment of this invention, the patient support device 103 may also be used with a conventional surgical table and may detect large body motions to avoid incorrect surgical treatment due to unexpected patient motions. According to an embodiment of this disclosure, the patient support device 103 may also be used with a standard bed located in a dwelling or in a healthcare setting (e.g., an intensive care unit (ICU)) and may perform continuous motioning of a patient's cardiac activity and/or respiration activity and/or other body motions to provide an indication of the patient's health condition.

Figure 7:
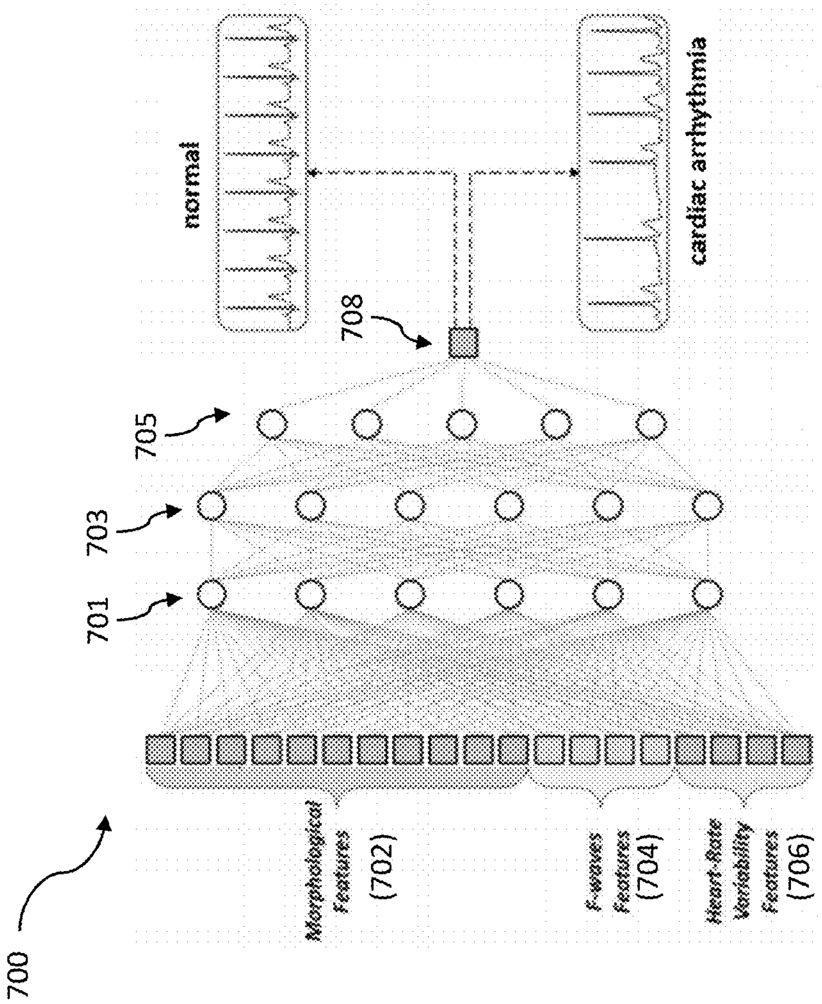
FIG. 7 schematically illustrates a machine learning process for cardiac arrhythmia identification based on an artificial neural network (ANN) according to various embodiments.

The electronical potentials/bio-impedance measured from a patient support device 103 in accordance with various embodiments may further be used as diagnosis tool to automatically detect cardiac arrhythmia and to trigger an imaging scan (e.g., a CT or MR image scan) with the assistance of machine learning process. The machine learning process may be a supervised or an unsupervised machine learning process. Supervised machine learning processes may include developing a predictive model using both input and desired output data. A supervised machine learning process may include classification, which includes mapping input data to discrete output labels or categories, or regression, which includes mapping input data to a continuous output. An unsupervised machine learning processes may include developing a predictive model using just input data. Unsupervised machine learning processes may include clustering and dimensionality reduction of the input data, which may produce discrete and/or continuous outputs. In various embodiments, the input and/or output data of a machine learning process may include electronical potentials/bio-impedance data measured from a patent support device 103 according to the present disclosure, and may be in the form of measured ECG and/or respiration activity signals. An initial step of a machine learning process may include signal acquisition based on electronical potentials/bio-impedance measurement. A pre-processing process may include removing noise and other outliers from the data set. A feature extraction process may include determining the spectrum of the data point groupings and the features to which they correspond. A feature selection process may include isolating desired classifiers that the machine learning method will be testing for following a training process. A machine learning training process may include using training data sets, either with or without known outputs, to refine a classification method. Lastly, a testing phase may include the processing of true test data sets and comparing the overall accuracy of the desired feature. FIG. 7 schematically illustrates a machine learning process for cardiac arrhythmia identification based on an artificial neural network (ANN) 700. The ANN 700 may include a three hidden layer architecture with 6 neurons in the first hidden layer 701, 6 neurons in the second hidden layer 703 and 5 neurons in the third hidden layer 705. In one non-limiting embodiment, the ANN may be fed with a set of nineteen (19) input features which may be automatically extracted from body surface electronical potentials/bio-impedance measurements. By considering the three criteria for cardiac arrhythmia diagnosis, the features set in this embodiment may include standard morphological features of ECG waves 702 (to reflect possible P-wave disappearance) as well as ECG features that typically characterize cardiac arrhythmia. The features set of the ANN 700 may also include F-waves features 704 to reflect possible F-waves appearance, and heart rate variability (HRV) features 706 to reflect possible HRV increment. The output 708 of the ANN 700 is the identification of ECG classification in terms of normal behaviour or cardiac arrhythmia. Unlike conventional techniques that include deploying an ANN on multiple heart anatomy images from CT or MR scans with much longer acquisition times and involving complex processes, the exemplary embodiment method based on bio-impedance measurement may be faster and less expensive.

Figure 8:
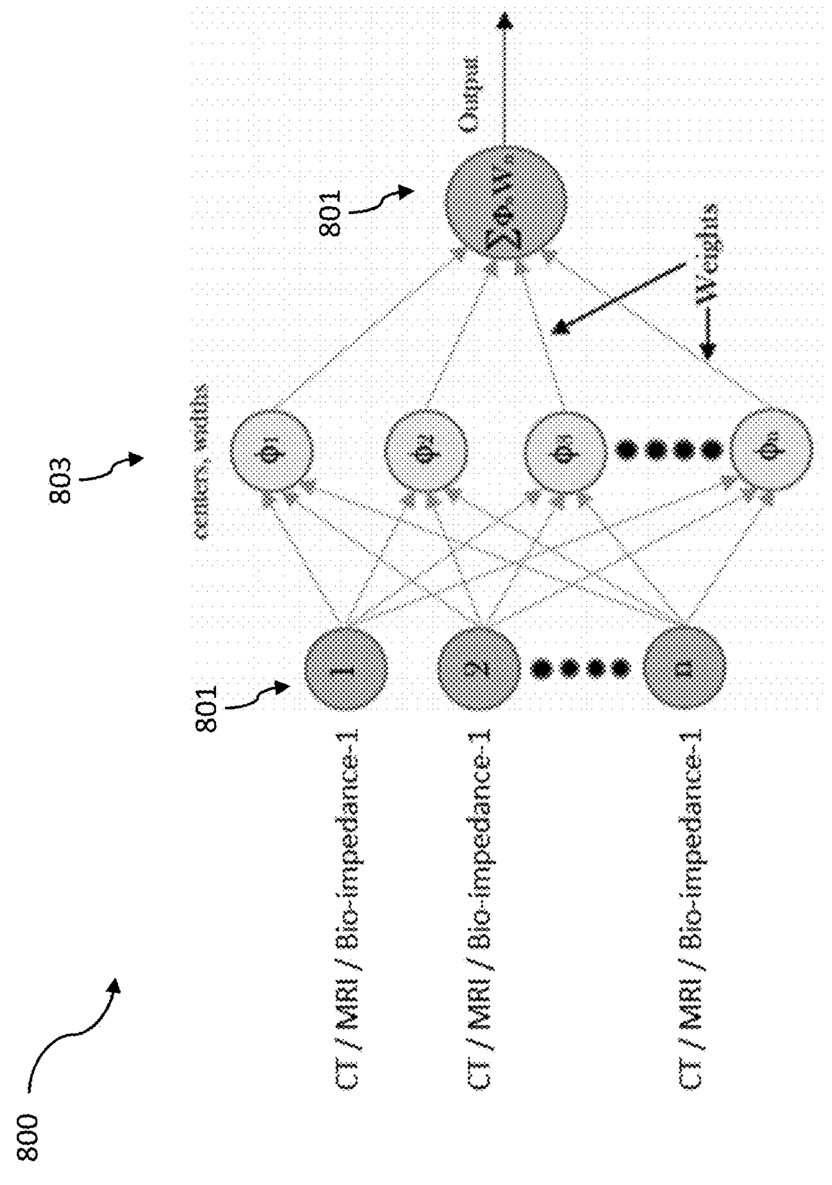
FIG. 8 schematically illustrates the general architecture of a radial basis function (RBF) network according to various embodiments.

A radial basis function (RBF) is one type of ANN. FIG. 8 shows the general architecture of an RBF network 800. The RBF network 800 of FIG. 8 includes three layers with entirely different roles. An input layer 801 may include source nodes that connect the network to its environment. A second layer 803 may be a hidden layer which may apply a nonlinear transformation from the input space to the hidden space, which is of high dimensionality. An output layer 805 may be linear, supplying the response of the network to the activation patterns applied to the input layer 801. Each RBF unit may have two parameters in terms of a center and a width. This center is used to compare the network input vector to produce a radially symmetrical response. The width controls the smoothness properties of the interpolating function. Responses of the hidden layer 803 are scaled by the connection weights of the output layer 805 and then combined to produce the network output. In the classical approach to RBF network implementation, the basic functions are usually chosen as Gaussian and the number of hidden units is fixed based on some properties of the input data. The weights connecting the hidden and output units may be estimated by a linear least squares method. In accordance with embodiments of the present disclosure, an RBF network such as shown in FIG. 8 may be used to predict certain motion states of cardiac and respiration activity based on the input data set from patient images (e.g., CT or MR scans) and measured bio-impedance/electrical potential data from the patient's body surface.

In various embodiments, a Principal Component Analysis (PCA) method may be used in signal processing for data reduction and feature extraction. PCA is a dimensionality reduction technique based on extracting the desired number of principal components of the multi-dimensional data. The purpose of PCA is to reduce the large dimensionality of the data space (e.g., multiple electronic potentials/bio-impedance measured from multiple electrodes) to the smaller intrinsic dimensionality of feature space (independent variables), which are needed to describe the data economically. The first principal component is the linear combination of the original dimensions that has the maximum variance; the nth principal component is the linear combination with the highest variance, subject to being orthogonal to the $n-1$ first principal components. Based on a PCA analysis, the processor 107 may generate control signal(s) configured to selectively de-active one or more selected electrodes on the patient's body surface such that overall electromagnetic noise may be reduced during an MR image scan to obtain high-quality images without electromagnetic noise interference. Since the PCA method may determine which electrodes are less relevant and may be de-activated, the deactivation of one or more electrodes will not disturb the accuracy of overall body motion detection such as cardiac activity and respiration activity.

Figure 9:
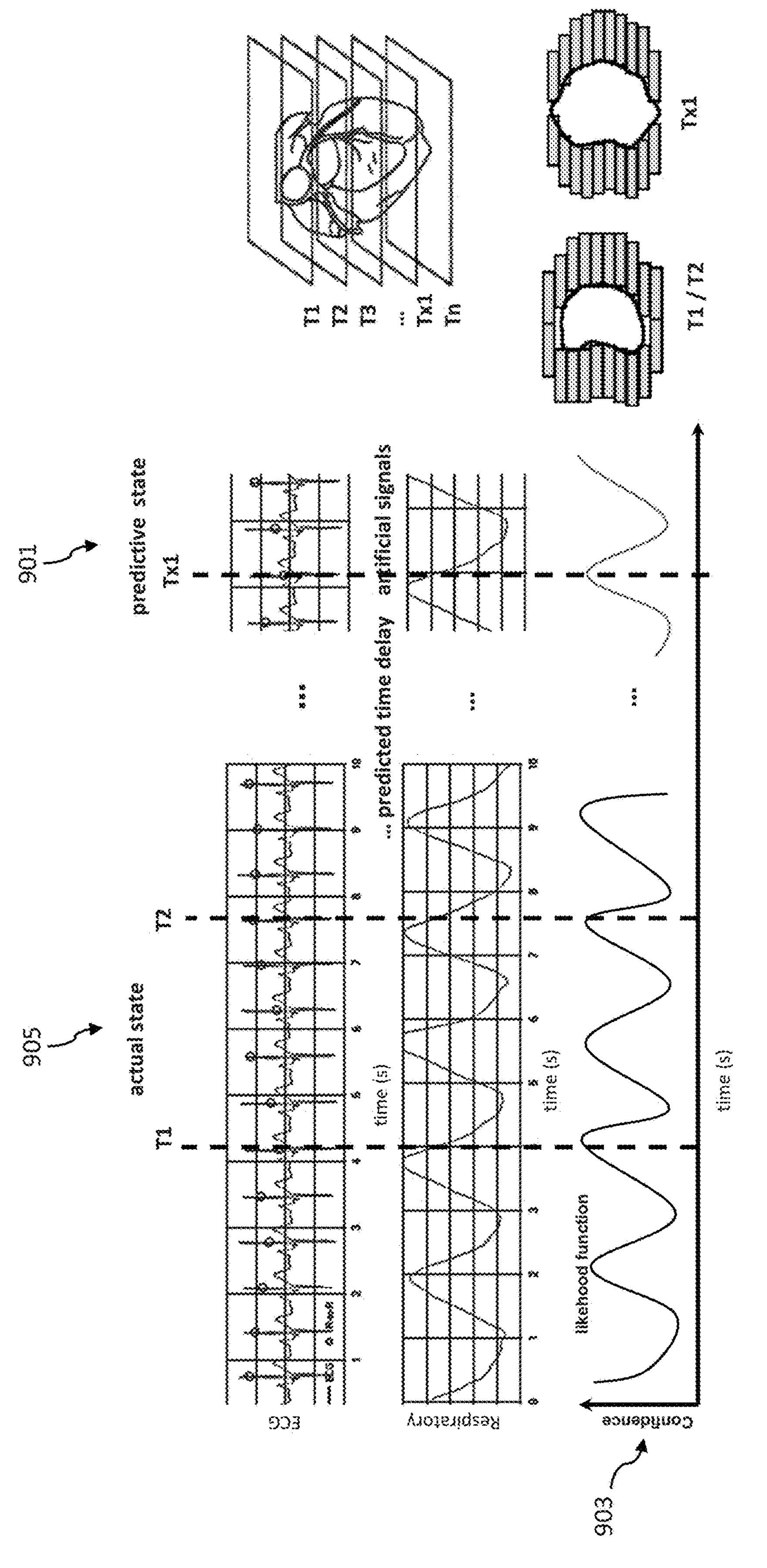
FIG. 9 schematically illustrates a method of using a predicative motion model for image scan and treatment according to various embodiments.

A combination of mathematical methods (e.g., PCA), statistical analysis, and machine learning methods may take advantage of the unique characteristics that each method possesses. This may provide a multimodal algorithm that is configured to extract additional desired features. The significance of multimodal integration is that it may allow for a higher-resolution classification than that of the individual methods separately. As illustrated FIG. 9, a PCA method may be applied on the patient's historical biological data such as ECG/respiration signals (e.g., in between T1 and T2) to extract unique characteristics and to identify correlations such that the processor 107 may generate artificial signals 901 to predict ECG/respiration state in the future even before actual measurement (e.g., at T×1 time). This may allow a user and/or the processor 107 sufficient time to adjust imaging scan, treatment planning, and/or radiation beam parameters ahead of time. The conventional technique provides treatment based on the actual anatomy images. However, embodiments of the present disclosure may provide treatment based on a prediction model. In addition, the processor 107 may also compare the actual measured data and prediction data such that it may further generate a likelihood function 903 as a confidence indication of a subsequent body motion prediction. If the confidence level of the likelihood function 903 is very low, then the processor 107 may generate control signals to trigger the radiation beam based on the actual measured signals 905. However, if the confidence level of the likelihood function 903 is sufficiently high, such as above a threshold value, the processor may generate control signals to trigger the radiation beam based on the prediction model 901.

Figure 10:
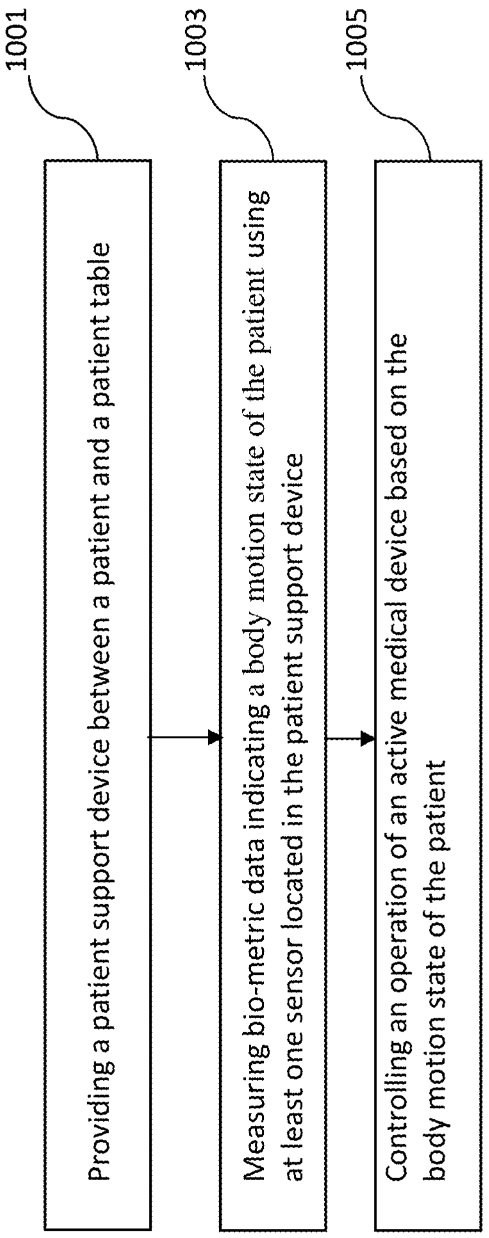
FIG. 10 illustrates a flowchart for a method of controlling a medical device according to one or more embodiments.

FIG. 10 illustrates a flowchart for a method of controlling a medical device according to one or more embodiments. As illustrated in FIG. 10, the method may include a step 1001, which includes providing a patient support device 103 between a patient 10 and a patient table 105. The method may further include a step 1003, which includes measuring bio-metric data indicating a body motion state of the patient 10 using at least one sensor 205 located in the patient support device 103. The method may further include a step 1005, which includes controlling an operation of an active medical device 109, 602 based on the body motion state of the patient 10.

Figure 11:
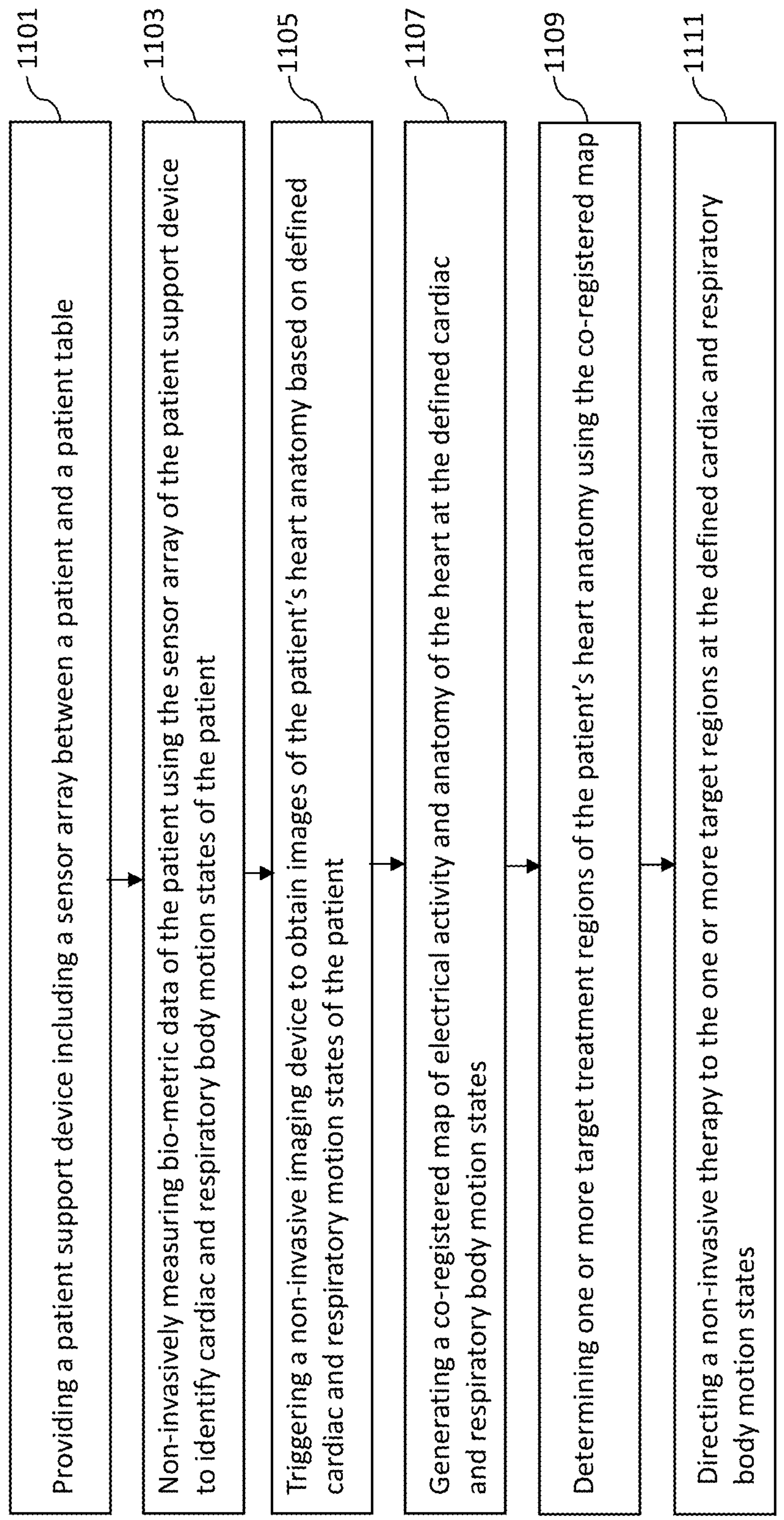
FIG. 11 illustrates a flowchart for a method of treating cardiac arrythmia according to one or more embodiments.

FIG. 11 illustrates a flowchart for a method of treating cardiac arrythmia according to one or more embodiments. As illustrated in FIG. 11, the method may include a step 1101, which includes providing a patient support device 103 including a sensor array between a patient 10 and a patient table 105. The method may further include a step 1103, which includes non-invasively measuring bio-metric data of the patient 10 using the sensor array of the patient support device 103 to identify cardiac and respiratory body motion states of the patient 10. The method may further include a step 1105, which includes triggering a non-invasive imaging device 602 to obtain images of the patient's heart anatomy based on defined cardiac and respiratory motion states of the patient 10. The method may further include a step 1107, which includes generating a co-registered map of electrical activity and anatomy of the heart at the defined cardiac and respiratory body motion states. The method may further include a step 1109, which includes determining one or more target treatment regions of the patient's heart anatomy using the co-registered map. The method may further include a step 1111, which includes directing a non-invasive therapy to the one or more target regions at the defined cardiac and respiratory body motion states.

Figure 12:
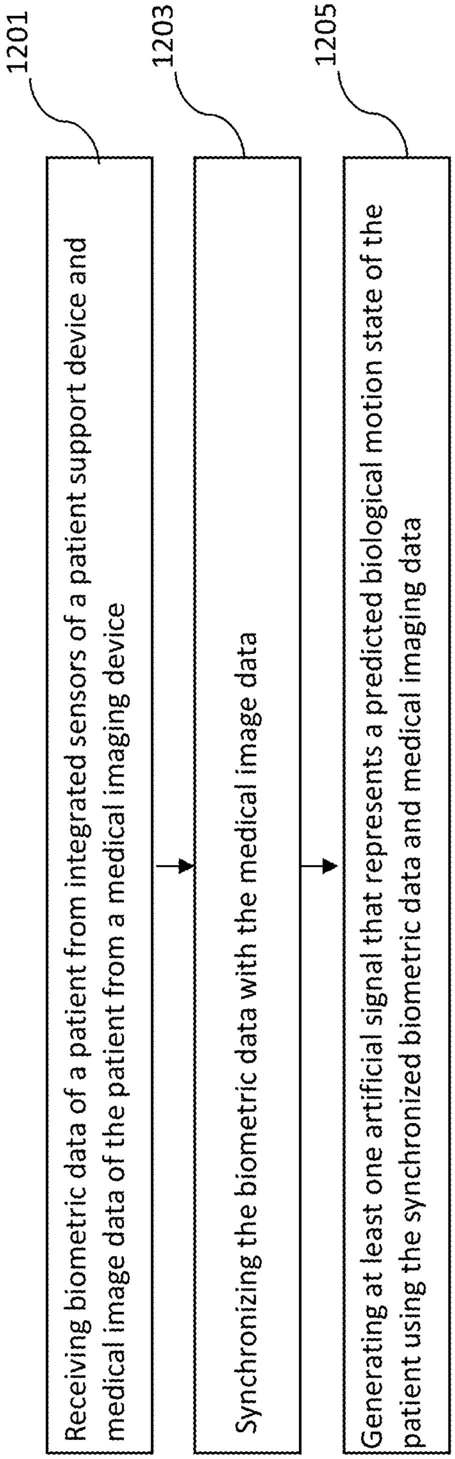
FIG. 12 illustrates a flowchart for a method for non-invasively determining a biological motion state inside the body of a patient according to one or more embodiments.

FIG. 12 illustrates a flowchart for a method for non-invasively determining a biological motion state inside the body of a patient according to one or more embodiments. As illustrated in FIG. 12, the method may include a step 1201, which includes receiving biometric data of a patient 10 from integrated sensors of a patient support device 103 and medical image data of the patient 10 from a medical imaging device 602. The method may further include a step 1203, which includes synchronizing the biometric data with the medical image data. The method may further include a step 1205, which includes generating at least one artificial signal that represents a predicted biological motion state inside the body of the patient 10 using the synchronized biometric data and medical imaging data.

Figure 13:
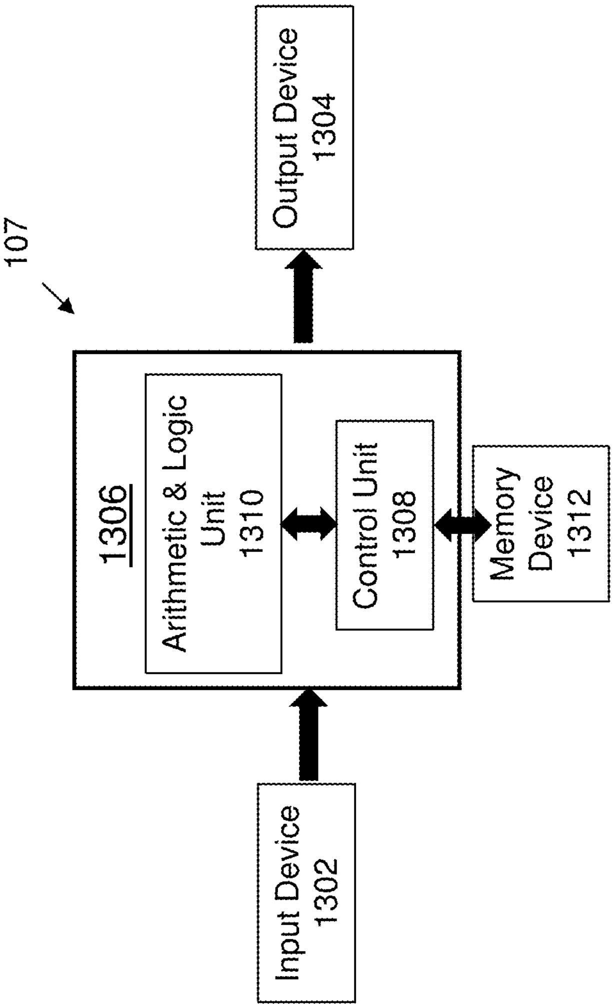
FIG. 13 is a schematic block diagram showing a processing device that may be used in accordance with various embodiments of the present disclosure.

In various embodiments, the various methods described herein may be implemented using a processing device (e.g., a computer) such as the processing device 700 shown in FIG. 1. FIG. 13 is a schematic block diagram showing a processing device 700 that may be used in accordance with various embodiments of the present disclosure. Referring to FIG. 13, a processing device 700 according to various embodiments may include an input device 1302 (e.g., a keyboard, mouse, touchscreen device, etc.) and an output device 1304 (e.g., a display device, printer, etc.) coupled to a processing unit 1306 (e.g., a central processing unit). In various embodiments, the input device 1302 may include a communication channel configured to receive biometric data, such as bio-impedance data, from one or more sensors 205 of a patient support device 103 as described above. In addition, the output device 1304 may include a communication channel with one or more active medical devices, such as a radiotherapy device and/or an imaging device. The processor 107 may be configured to transmit control signals for controlling the operation of the one or more active medical devices over the communication channel. The processing unit 1306 may include a control unit 1308 and an arithmetic and logic unit (ALU) 1310 and may be coupled to a memory device 1312 (e.g., a random access memory (RAM)) that is configured with processor-executable instructions for performing the operations of the various methods described herein.

Referring to all drawings and according to various embodiments of the present disclosure, implementation examples are described in the following paragraphs.

Example 1. A system 100 for monitoring a body motion state of a patient includes a patient support device 103 including at least one sensor (205, 301) for measuring biometric data of a patient 10 located on the patient support device 103, and a processor 107, operatively coupled to an active medical device (109, 602) and the at least one sensor (205, 301) of the patient support device 103, the processor 107 containing processor-executable instructions configured to perform operations including generating a control signal to control an operation of an active medical device (109, 602) based on the biometric data measured by the at least one sensor (205, 301), wherein the biometric data indicates a body motion state of the patient 10.

Example 2. A system 100 according to Example 1, in which the body motion state of the patient 10 includes at least one of cardiac activity and respiratory activity of the patient 10.

Example 3. A system 100 according to any of Examples 1-2, in which the active medical device (109, 206) includes one or more of a magnetic resonance imaging (MRI) device, an X-ray device, a computed tomography (CT) device, an ultrasonography device, a radiotherapy device, a shockwave generator, a positron emission tomography (PET) device, an ElectroCardioGraphic imaging (ECGi) device, and a high-intensity focused ultrasound device.

Example 4. A system 100 according to any of Examples 1-3, in which the patient support device 103 is located between an upper surface of a patient table 105 and a patient 10 supported on the patient table 105.

Example 5. A system 100 according to any of Examples 1-4, in which the patient support device 103 includes at least one non-conductive material that does not generate image artifacts during an X-Ray scan and/or an MRI scan.

Example 6. A system 100 according to any of Examples 1-5, in which the patient support device 103 includes a mouldable vacuum cushion including a flexible bag of gas-impermeable material.

Example 7. A system 100 according to any of Examples 1-6, in which the at least one sensor (205, 301) of the patient support device 103 includes one or more of an accelerometer, a gyroscope, an inclinometer, and a photoplethysmogram sensor to provide physic motion parameters as part of the biometric data of the patient 10.

Example 8. A system 100 according to any of Examples 1-7, in which the at least one sensor (205, 301) of the patient support device 103 includes at least two skin-electrode interfaces for measuring electronic potentials from the body of the patient 10.

Example 9. A system 100 according to any of Examples 1-8, in which the at least one sensor (205, 301) of the patient support device 103 includes an electrode array with more than two skin-electrode interfaces for measuring multiple electronic potentials across the body of the patient 10.

Example 10. A system 100 according to any of Examples 1-9, in which each of the at least two skin-electrode interfaces includes an electrode 301 selected from a wet-contact gel-based Ag/AgCl electrode, a dry-contact MEMS and metal plate electrode, a thin-film insulated metal plate electrode, a flexible electrode and a stretchable electrode.

Example 11. A system 100 according to any of Examples 1-10, in which the at least one sensor (205, 301) includes a sensor unit 205 coupled to the electrodes 301 of the at least two skin-electrode interfaces by respective interconnections 303, where each of the interconnections 303 is located inside of the patient support device 103 and includes a flexible and stretchable printed circuit board (PCB), or a flexible and stretchable cable, or a printed conductive signal trace that is located on an interior surface of a cover of the patient support device 103.

Example 12. A system 100 according to any of Examples 1-11 in which the processor 107 is configured with processor-executable instructions to perform operations further including generating control signals to individually activate and de-activate selected electrodes 301 of the at least two skin-electrode interfaces.

Example 13. A system 100 according to any of Examples 1-12 in which the biometric data includes bio-impedance data derived from measured electrical potentials, and the processor 107 is configured with processor-executable instructions to perform operations further including determining an estimated body composition of the patient 10 based on the bio-impedance data.

Example 14. A system 100 according to any of Examples 1-13 in which the biometric data includes bio-impedance data derived from measured electrical potentials, and the processor 107 is configured with processor-executable instructions to perform operations further including analyzing a galvanic skin response of the patient 10 based on the bio-impedance data to determine a stress level of the patient 10.

Example 15. A system 100 according to any of Examples 1-14 in which the biometric data includes time-variable bio-impedance data derived from measured electrical potentials that indicate at least one of cardiac activity and respiration activity of the patient 10.

Example 16. A system 100 according to any of Examples 1-15 in which the active medical device includes a diagnostic imaging device 206, and the control signal generated by the processor 107 is configured to enable or disable a diagnostic imaging procedure by the diagnostic imaging device 206.

Example 17. A system 100 according to any of Examples 1-15 in which the active medical device includes a radiotherapy device 109, and the control signal generated by the processor 107 is configured to enable or disable a delivery of a radiation beam from the radiotherapy device 109.

Example 18. A system 100 according to any of Examples 1-17 in which the processor 107 transmits the control signal to the active medical device (109, 206) via at least one of an optical communication channel using optical fibers or a wireless communication channel.

Example 19. A method of controlling a medical device that includes providing a patient support device 103 between a patient 10 and a patient table 105, measuring biometric data indicating a body motion state of the patient 10 using at least one sensor (205, 301) located in the patient support device 103, and controlling an operation of an active medical device (109, 206) based on the body motion state of the patient 10.

Example 20. A method according to Example 19 in which the active medical device (109, 206) includes one or more of a magnetic resonance imaging (MRI) device, an X-ray device, a computed tomography (CT) device, an ultrasonography device, a radiotherapy device, a shockwave generator, a positron emission tomography (PET) device, an ElectroCardioGraphic imaging (ECGi) device, and a high-intensity focused ultrasound device.

Example 21. A method according to any of Examples 19-20 in which the body motion state of the patient 10 includes at least one of cardiac activity and respiratory activity of the patient 10.

Example 22. A method of treating cardiac arrythmia that includes providing a patient support device 103 including a sensor array (205, 301) between a patient 10 and a patient table 105, non-invasively measuring biometric data of the patient 10 using the sensor array (205, 301) of the patient support device 103 to identify cardiac and respiratory body motion states of the patient 10, triggering a non-invasive imaging device 206 to obtain images of the patient's heart anatomy based on defined cardiac and respiratory motion states of the patient 10, generating a co-registered map of electrical activity and anatomy of the heart at the defined cardiac and respiratory body motion states, determining one or more target treatment regions of the patient's heart anatomy using the co-registered map, and directing a non-invasive therapy to the one or more target regions at the defined cardiac and respiratory body motion states.

Example 23. A method according to Example 22 in which the non-invasive therapy includes one of more of stereotactic radiosurgery, stereotactic body radiotherapy, stereotactic ablative radiotherapy, fractionated radiotherapy, hypofractionated radiotherapy, and high-intensity focused ultrasound.

Example 24. A method according to any of Examples 22-23 in which the integrated sensor array (205, 301) includes skin-electrode interfaces configured to measure electrical potentials at a plurality of locations on the patient 10.

Example 25. A method according to any of Examples 22-24, in which the biometric data measured using the integrated sensor array (205, 301) is used to identify an arrythmia.

Example 26. A method according to any of Examples 22-25 in which the arrythmia is identified using the biometric data and a machine learning process.

Example 27. A method according to any of Examples 22-26 in which the patient 10 is located on a patient support device 103 including a sensor array (205, 301) during the non-invasive therapy, and the method further includes non-invasively measuring biometric data of the patient 10 using the sensor array (205, 301) of the patient support device 103 to identify cardiac and respiratory body motion states of the patient 10 during the non-invasive therapy, and triggering a non-invasive therapy device 109 to direct the non-invasive therapy to the one or more target regions at the defined cardiac and respiratory body motion states, wherein the defined cardiac and respiratory body motion states are the same cardiac and respiratory motion states at which the images of the patient's heart anatomy are obtained by the non-invasive imaging device 206.

Example 28. A non-invasive method for determining a biological motion state inside the body of a patient 10 that includes receiving biometric data from integrated sensors (205, 301) of a patient support device 103 and medical image data from medical imaging device 206, synchronizing the biometric data with the medical image data, and generating at least one artificial signal that represents a predicted biological motion state inside the body of the patient using the synchronized biometric data and medical imaging data.

Example 29. A non-invasive method according to Example 28, in which the predicted biological motion state is identified based on a principal component analysis.

Example 30. A non-invasive method according to any of Examples 28-29 in which the artificial signal is generated using a machine learning process.

Example 31. A non-invasive method according to any of Examples 28-30 in which the machine learning process is an empirical learned model that combines features from a set of features with respective learned weights.

Example 32. A non-invasive method according to any of Examples 28-31, in which the machine learning process includes a regression function trained using image-based boosting ridge regression.

Example 33. A non-invasive method according to any of Examples 28-32, further including controlling an operation of a medical device (109, 206) based on the artificial signal when a confidence level of the predicted biological motion state is above a threshold level.

Embodiments of the present disclosure may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, 2G, 3G, 4G, 5G, 6G, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Embodiments of the present disclosure may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Embodiments of the present disclosure may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. Various embodiments of the present disclosure include variations on described embodiments that would be apparent to the skilled addressee, including variations obtained by: replacing features, elements and/or acts with equivalent features, elements and/or acts; mixing and matching of features, elements and/or acts from different described embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed:

1. A system for monitoring a body motion state of a patient, comprising:

a patient support device including at least one sensor for measuring biometric data of a patient, the at least one sensor located on the patient support device, wherein the patient support device and the at least one sensor located on the patient support device are configured to be located between an upper surface of a patient table and a patient supported on the patient table, and the patient support device comprises a mouldable vacuum cushion comprising a flexible bag of gas-impermeable material, the at least one sensor located on the mouldable vacuum cushion, and the mouldable vacuum cushion is mouldable to an outline shape of the patient to enable the at least one sensor to be repeatedly positioned in the same position with respect to the patient; and a processor, operatively coupled to an active medical device and the at least one sensor of the patient support device, the processor containing processor-executable instructions configured to perform operations comprising:

generating a control signal to control an operation of the active medical device to perform imaging and/or treatment of an internal anatomy of the patient based on the biometric data measured by the at least one sensor, wherein the biometric data indicates a body motion state of the patient comprising at least one of cardiac activity and respiratory activity of the patient.

2. The system of claim 1, wherein the active medical device comprises one or more of a magnetic resonance imaging (MRI) device, an X-ray device, a computed tomography (CT) device, an ultrasonography device, a radiotherapy device, a shockwave generator, a positron emission tomography (PET) device, an ElectroCardioGraphic imaging (ECGi) device, and a high-intensity focused ultrasound device.

3. The system of claim 1, wherein the patient support device comprises at least one non-conductive material that does not generate image artifacts during an X-Ray scan and/or an MRI scan.

4. The system of claim 1, wherein the at least one sensor of the patient support device comprises one or more of an accelerometer, a gyroscope, an inclinometer to provide physics motion parameters, and a photoplethysmogram sensor to provide physiological motion parameters as part of the biometric data of the patient.

5. The system of claim 1, wherein the at least one sensor of the patient support device comprises at least two skin-electrode interfaces for measuring electronic potentials from the body of the patient.

6. The system of claim 5, wherein the at least one sensor of the patient support device comprises an electrode array with more than two skin-electrode interfaces for measuring multiple electronic potentials across the body of the patient.

7. The system of claim 5, wherein each of the at least two skin-electrode interfaces comprises an electrode selected from a wet-contact gel-based Ag/AgCl electrode, a dry-contact MEMS and metal plate electrode, a thin-film insulated metal plate electrode, a flexible electrode and a stretchable electrode.

8. The system of claim 5, wherein the at least one sensor comprises a sensor unit coupled to the electrodes of the at least two skin-electrode interfaces by respective interconnections, wherein each of the interconnections is located inside of the patient support device and comprises a flexible and stretchable printed circuit board (PCB), or a flexible and stretchable cable, or a printed conductive signal trace that is located on an interior surface of a cover of the patient support device.

9. The system of claim 5, wherein the processor is configured with processor-executable instructions to perform operations further comprising:

generating control signals to individually activate and de-activate selected electrodes of the at least two skin-electrode interfaces.

10. The system of claim 1, wherein the biometric data comprises bio-impedance data derived from measured electrical potentials, and the processor is configured with processor-executable instructions to perform operations further comprising:

determining an estimated body composition of the patient based on the bio-impedance data.

11. The system of claim 1, wherein the biometric data comprises bio-impedance data derived from measured electrical potentials, and the processor is configured with processor-executable instructions to perform operations further comprising:

analyzing a galvanic skin response of the patient based on the bio-impedance data to determine a stress level of the patient.

12. The system of claim 1, wherein the biometric data comprises time-variable bio-impedance data derived from measured electrical potentials that indicate at least one of cardiac activity and respiration activity of the patient.

13. The system of claim 1, wherein the active medical device comprises a diagnostic imaging device, and the control signal generated by the processor is configured to enable or disable a diagnostic imaging procedure by the diagnostic imaging device.

14. The system of claim 1, wherein the active medical device comprises a radiotherapy device, and the control signal generated by the processor is configured to enable or disable a delivery of a radiation beam from the radiotherapy device.

15. The system of claim 1, wherein the processor transmits the control signal to the active medical device via at least one of an optical communication channel using optical fibers or a wireless communication channel.

16. The system of claim 1, wherein:

the at least one sensor comprises a sensor array between the patient and the patient table, wherein the system is configured to:

non-invasively measure biometric data of the patient using the sensor array of the patient support device to identify cardiac and respiratory body motion states of the patient;

trigger a non-invasive imaging device to obtain images of the patient's heart anatomy based on defined cardiac and respiratory motion states of the patient;

generate a co-registered map of electrical activity and anatomy of the heart at the defined cardiac and respiratory body motion states; and determine one or more target treatment regions of the patient's heart anatomy using the co-registered map, wherein the processor generates the control signal to control the active medical device to direct a non-invasive therapy to the one or more target regions at the defined cardiac and respiratory body motion states.

17. The system of claim 16, wherein the non-invasive therapy comprises one of more of stereotactic radiosurgery, stereotactic body radiotherapy, stereotactic ablative radiotherapy, fractionated radiotherapy, hypofractionated radiotherapy, and high-intensity focused ultrasound.

18. The system of claim 16, wherein the sensor array comprises skin-electrode interfaces configured to measure electrical potentials at a plurality of locations on the patient.

19. The system of claim 16, wherein the system uses biometric data measured using the sensor array to identify an arrythmia.

20. The system of claim 19, wherein the arrythmia is identified using the biometric data and a machine learning process.

21. The system of claim 16, wherein the patient support device including the sensor array is configured to support the patient during the non-invasive therapy, and the system is further configured to:

non-invasively measure biometric data of the patient using the sensor array of the patient support device to identify cardiac and respiratory body motion states of the patient during the non-invasive therapy, wherein the processor generates the control signal to trigger a non-invasive therapy device to direct the non-invasive therapy to the one or more target regions at the defined cardiac and respiratory body motion states, wherein the defined cardiac and respiratory body motion states are the same cardiac and respiratory motion states at which the images of the patient's heart anatomy are obtained by the non-invasive imaging device.

22. The system of claim 1, wherein the at least one sensor comprises integrated sensors of the patient support device, wherein the system is configured to:

receive biometric data from the integrated sensors of the patient support device and medical image data from a medical imaging device;

synchronize the biometric data with the medical image data; and generate at least one artificial signal that represents a predicted periodically reproducible biological motion state of the body of the patient using the synchronized biometric data and medical imaging data.

23. The system of claim 22, wherein the predicted periodically reproducible biological motion state is identified based on a principal component analysis.

24. The system of claim 22, wherein the artificial signal is generated using a machine learning process.

25. The system of claim 24, wherein the machine learning process is an empirical learned model that combines features from a set of features with respective learned weights.

26. The system of claim 24, wherein the machine learning process comprises a regression function trained using image-based boosting ridge regression.

27. The system of claim 22, wherein the system is further configured to:

control an operation of a medical device based on the artificial signal when a confidence level of the predicted periodically reproducible biological motion state is above a threshold level.

28. The system of claim 1, wherein the at least one sensor comprises a skin-electrode interface array located at predefined positions on the mouldable vacuum cushion for directly measuring electronic potentials from the body surface of the patient.

29. The system of claim 28, wherein interconnections between the skin-electrode interface array and the processor comprise a flexible and stretchable printed circuit board (PCB), or a flexible and stretchable cable, or a printed conductive signal trace disposed inside the mouldable vacuum cushion or on an interior surface of a cover of the patient support device, wherein said interconnections are configured to deform with the mouldable vacuum cushion.

30. The system of claim 29, wherein the biometric data comprises time-variable bio-impedance data derived from measured electrical potentials that indicate at least one of cardiac activity and respiration activity of the patient.

31. A system for monitoring a body motion state of a patient, comprising:

a patient support device including at least one sensor for measuring biometric data of a patient, the at least one sensor located on the patient support device, wherein the patient support device comprises a mouldable vacuum cushion comprising a flexible bag of gas-impermeable material and the at least one sensor comprises at least two skin-electrode interfaces for directly measuring electronic potentials from the body surface of the patient, and the mouldable vacuum cushion is configured to be mouldable to an outline shape of the patient to enable the skin-electrode interfaces to be repeatedly positioned in the same position with respect to the patient; and a processor, operatively coupled to an active medical device and the at least one sensor of the patient support device, the processor containing processor-executable instructions configured to perform operations comprising:

generating a control signal to control an operation of the active medical device to perform imaging and/or treatment of an internal anatomy of the patient based on the biometric data measured by the at least one sensor, wherein the biometric data indicates a body motion state of the patient.

* * * * *